United States Patent
Lele et al.

(10) Patent No.: US 10,259,969 B2
(45) Date of Patent: Apr. 16, 2019

(54) PARAMAGNETIC SUPPORTS FOR USE AS ASSAY REAGENTS

(71) Applicant: Siemens Healthcare Diagnostics Inc., Tarrytown, NY (US)

(72) Inventors: Bhalchandra S. Lele, Newark, DE (US); Eric Allgaier, Wake Forest, NC (US); Robert Pervere, Stamford, CT (US); Jeremy Lyons, Newark, DE (US); Steve St-Onge, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/110,372

(22) Filed: Aug. 23, 2018

(65) Prior Publication Data

US 2018/0362796 A1  Dec. 20, 2018

Related U.S. Application Data

(62) Division of application No. 15/113,920, filed as application No. PCT/US2015/013479 on Jan. 29, 2015, now Pat. No. 10,077,376.

(60) Provisional application No. 61/934,111, filed on Jan. 31, 2014.

(51) Int. Cl.
| | |
|---|---|
| C09D 133/26 | (2006.01) |
| C07C 233/20 | (2006.01) |
| C09D 133/24 | (2006.01) |
| C09D 123/08 | (2006.01) |
| G01N 33/82 | (2006.01) |
| C08F 2/06 | (2006.01) |
| C08F 230/02 | (2006.01) |
| G01N 33/78 | (2006.01) |
| C08F 220/58 | (2006.01) |

(52) U.S. Cl.
CPC .......... *C09D 133/26* (2013.01); *C07C 233/20* (2013.01); *C08F 2/06* (2013.01); *C08F 220/58* (2013.01); *C08F 230/02* (2013.01); *C09D 123/0869* (2013.01); *C09D 133/24* (2013.01); *G01N 33/78* (2013.01); *G01N 33/82* (2013.01); *C08F 2800/10* (2013.01)

(58) Field of Classification Search
CPC ............ C09D 123/0869; C09D 133/26; C09D 133/24; C08F 2/06; C08F 220/58; C08F 230/02; C08F 220/20; C08F 220/06; C08F 2800/10; C08F 2220/286; C08F 2220/387; C07C 233/20; G01N 33/78; G01N 33/82

See application file for complete search history.

(56) References Cited

U.S. PATENT DOCUMENTS

| | | |
|---|---|---|
| 7,713,541 B1 | 5/2010 | Pacetti et al. |
| 8,048,659 B1 | 11/2011 | Leif et al. |
| 2006/0083858 A1 | 4/2006 | Barden et al. |
| 2008/0139399 A1 | 6/2008 | Fonnum et al. |
| 2010/0137133 A1 | 6/2010 | Maeno et al. |
| 2012/0276608 A1 | 11/2012 | Chang et al. |
| 2013/0345357 A1 | 12/2013 | Lele et al. |

FOREIGN PATENT DOCUMENTS

EP  2422977 A1  2/2012

OTHER PUBLICATIONS

European Search Report and Written Opinion of European Application No. 15743428.3 dated Dec. 13, 2016.
International Search Report and Written Opinion of International Application No. PCT/US2015/013479 dated Apr. 15, 2015.
European Written Opinion of European Application No. 15743428.3 dated Jun. 1, 2018.

*Primary Examiner* — Shafiqul Haq
(74) *Attorney, Agent, or Firm* — Cynthia G. Tymeson

(57) ABSTRACT

A composition for use as an assay reagent includes a paramagnetic solid support comprising a coating of a synthetic copolymer. The synthetic copolymer comprises two or three of a first copolymerized monomer, a second copolymerized monomer and a third copolymerized monomer and further comprises a polyethylenic backbone.

6 Claims, 10 Drawing Sheets

Preparation of poly(AA-co-MA-Actl)

Preparation of copolymer-coated PMP - anti-FITC conjugates

PARAMAGNETIC SUPPORTS FOR USE AS ASSAY REAGENTS

This is a divisional application U.S. Ser. No. 15/113,920, filed Jul. 25, 2016 which claims the benefit of US National Stage of International Application No. PCT/US2015/013479, filed Jan. 29, 2015 and claims priority under 35 U.S.C. 119(e) to U.S. Provisional Application No. 61/934,111, filed Jan. 31, 2014. All of the applications are incorporated by reference herein in their entirety.

BACKGROUND

The present invention relates generally to copolymer-coated solid supports and, more particularly, to compositions useful as assay reagents.

Aldehyde-coated paramagnetic particles are useful as reagents in assays. However, aldehyde-coated paramagnetic particles, for example, paramagnetic particles coated with glutaraldehyde, exhibit undesirable instability during storage. Polystyrene latex magnetic particles may be employed in assays, but such particles are more expensive than paramagnetic particles.

There is a need for a coating to be used on the surface of paramagnetic particles for linking various moieties to the particles where the resultant particles have enhanced stability during storage.

SUMMARY

One example in accordance with the principles described herein is a composition for use as an assay reagent. The composition comprises a paramagnetic solid support and a coating of a synthetic copolymer. The synthetic copolymer comprises two or three of a first copolymerized monomer, a second copolymerized monomer and a third copolymerized monomer and further comprises a polyethylenic backbone. The first copolymerized monomer comprises a pendant moiety of the formula:

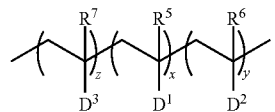

wherein:
R$^1$ is H or alkyl of from 1 to 6 carbon atoms,
X is O or NR$^2$ wherein R$^2$ is H or alkyl of from 1 to 6 carbon atoms,
Z is H or alkyl of from 1 to 6 carbon atoms,
m is 1 to 100,
R$^3$ and R$^4$ are independently H or alkyl of from 1 to 6 carbon atoms,
R$^{11}$, R$^{12}$ and R$^{13}$ are independently H or alkyl of from 1 to 6 carbon atoms,
p is 1 to 10,
q is 1 to 10,
r is 1 to 10,
s is 1 to 10,
t is 1 to 10.

The second copolymerized monomer comprises a pendant moiety of the formula:
(a) —C(O)-A-(CH$_2$)n-G wherein A is O or NR wherein R is H or alkyl of from 1 to 6 carbon atoms and n is 1 to 10 and wherein G is CHO; CH(OR$^8$)$_2$ wherein R$^8$ is alkyl of from 1 to 6 carbon atoms; COOH or a derivative thereof, OH; or a member of a specific binding pair; or (b) —OC(O)NR-J wherein R is H or alkyl of from 1 to 6 carbon atoms and J is a member of a specific binding pair. The third copolymerized monomer comprises a pendant moiety of the formula: —COOH or a derivative thereof. When the first copolymerized monomer is —C(O)—X—(CH$_2$)$_p$—CH(OH)—R$^1$ wherein R$^1$ is other than H, the synthetic copolymer comprises the second copolymerized monomer and the third copolymerized monomer.

Another example in accordance with the principles described herein is a method of determining in a sample one or both of the presence and the amount of an analyte. A combination is provided in a medium. The combination comprises the sample, a member of a signal producing system that is bound to a member of a specific binding pair that binds to the analyte or that is bound to an analyte analog, and a composition comprising a paramagnetic particle that comprises a member of a specific binding pair, which binds to the analyte, or to a member of a specific binding pair that binds to the analyte, to form a complex related to the presence of the analyte, and a coating of a synthetic copolymer. The synthetic copolymer comprises two or three of a first copolymerized monomer, a second copolymerized monomer and a third copolymerized monomer as described above. The combination is subjected to conditions for forming the complex and the paramagnetic particle is separated from the medium by, for example, by magnetic separation. The member of the signal producing system is activated and the amount of the complex is detected. The amount of the complex is related to one or both of the presence and the amount of analyte in the sample.

Another example in accordance with the principles described herein is a copolymer of the formula:

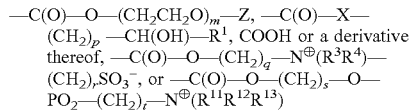

wherein:
D$^1$ is —C(O)—O—(CH$_2$CH$_2$O)$_m$—Z, —C(O)—X—(CH$_2$)$_p$—CH(OH)—R$^1$, COOH or a derivative thereof, —C(O)—O—(CH$_2$)$_q$—N$^⊕$(R$^3$R$^4$)—(CH$_2$)$_r$—SO$_3^-$, or —C(O)—O—(CH$_2$)$_s$—O—PO$_2$—(CH$_2$)$_t$—N$^⊕$(R$^{11}$R$^{12}$R$^{13}$)
wherein:
X is O or NR$^2$ wherein R$^2$ is H or alkyl of from 1 to 6 carbon atoms,
Z is H or alkyl of from 1 to 6 carbon atoms,
R$^1$ is H or alkyl of from 1 to 6 carbon atoms,
m is 1 to 100,
R$^3$ and R$^4$ are independently H or alkyl of from 1 to 6 carbon atoms,
R$^{11}$, R$^{12}$ and R$^{13}$ are independently H or alkyl of from 1 to 6 carbon atoms,
p is 1 to 10,
q is 1 to 10,
r is 1 to 10,
s is 1 to 10,
t is 1 to 10, and
D$^2$ is
(a) —C(O)-A-(CH$_2$)$_n$-G wherein A is O or NR wherein R is H or alkyl of from 1 to 6 carbon atoms and n is 1 to 10 and wherein G is CHO; CH(OR$^8$)$_2$ wherein R$^8$ is alkyl of from 1 to 6 carbon atoms; COOH or a derivative thereof; OH; or a member of a specific binding pair; or (b) —OC(O)NR-J wherein R is H or alkyl of from 1 to 6 carbon atoms and J is a member of a specific binding pair; and;

$D^3$ is —COOH or a derivative thereof;

$R^5$, $R^6$ and $R^7$ are independently H or alkyl of from 1 to 6 carbon atoms;

x is 1 to about 1000;

y is 1 to about 1000; and z is 0 or 1 to about 1000, with the proviso that z is not 0 when $D^1$ is —C(O)—NH—$(CH_2)_p$—CH(OH)—$R^1$ wherein $R^1$ is other than H.

DETAILED DESCRIPTION OF SPECIFIC EMBODIMENTS

Compositions

Figure 1:
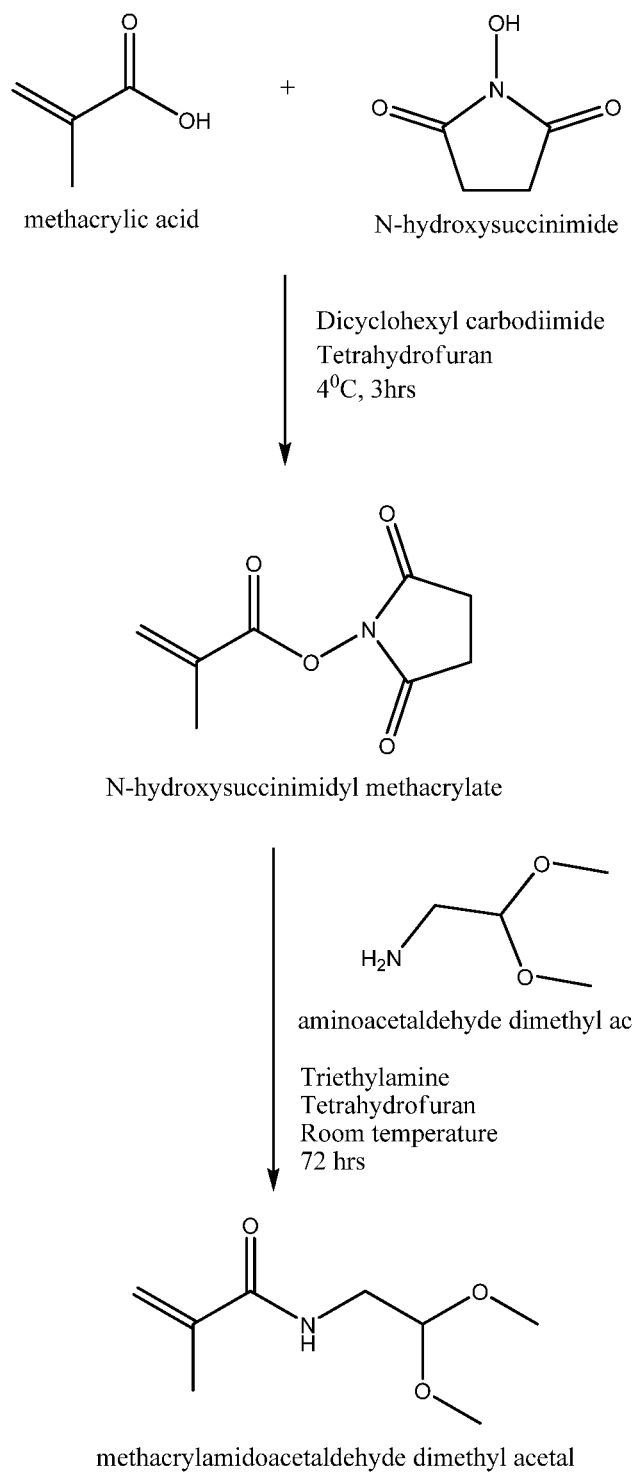
FIG. 1 is a schematic diagram of a synthesis of MAM-DMA.

In some examples in accordance with the principles described herein, the synthetic copolymer is a random copolymer comprising two or three copolymerized monomers. The synthetic copolymer is employed as a coating on the surface of paramagnetic solid supports. One of the monomer units of the copolymer comprises reactive functionalities for conjugation to molecules of interest such as, for example, a paramagnetic solid support or a member of a specific binding pair ("sbp member). Paramagnetic solid supports coated with synthetic copolymers in accordance with the principles described herein exhibit enhanced stability for use in assays when compared to other coatings. The synthetic copolymer coatings provide a less expensive alternative for paramagnetic solid supports over other solid supports such as, for example, latex magnetic particles.

In a random copolymer the distribution of the copolymerized monomers may be such that at any point in the polymer chain a first copolymerized monomer, a second copolymerized monomer and, if present, a third copolymerized monomer may alternate or may repeat as distinguished from block copolymers.

The monomers from which the copolymer is formed include, by way of example and not limitation, vinyl monomers, allylic monomers, olefins, and any small molecules containing at least one degree of unsaturation, and mixtures or two or more of the above monomers wherein the polymerizable functionality is a carbon-carbon double bond or a carbon-carbon triple bond. Classes of vinyl monomers include, but are not limited to, methacrylic acid, methacrylates, methacrylamide, N- and N,N-disubstituted methacrylamides, vinyl aromatic monomers, vinyl halides, vinyl esters of carboxylic acids (e.g., vinyl acetate), ethylene oxide acrylates, diacrylates, and dimethacrylates.

Examples of methacrylates include methacrylates appropriately substituted with a pendant moiety in accordance with present embodiments wherein the methacrylates include, by way of illustration and not limitation, methyl methacrylate, ethyl methacrylate, propyl methacrylate, isopropyl methacrylate, n-butyl methacrylate, iso-butyl methacrylate, and tert-butyl methacrylate, for example. Examples of vinyl aromatic monomers that may be used include, but are not limited to, appropriately substituted styrene, styrene-butadiene, p-chloromethylstyrene and divinyl benzene, for example. Vinyl halides that may be used include, but are not limited to, appropriately substituted vinyl chloride and vinylidene fluoride. Vinyl esters of carboxylic acids that may be used include, but are not limited to, appropriately substituted vinyl acetate, vinyl butyrate, vinyl 3,4-dimethoxybenzoate, vinyl malate and vinyl benzoate.

In some embodiments the number of each different copolymerized monomer in the copolymer is controlled during the preparation of the functionalized polymer by controlling the molar concentration of the monomer units that are employed in the preparation of the synthetic copolymer. Thus, the number of each of the copolymerized monomers (x, y and z in the formulas herein) is controlled in the final functionalized copolymer. The copolymer may be tailored, for example, to one or more of a particular paramagnetic solid support, to compositions comprising such supports and to the use of such composition.

The term "monomer" or "monomer unit" means a molecule capable of undergoing polymerization to form a polymer; the molecule comprises a polymerizable functionality. The number of monomer units depends on one or more of the number of atoms in the monomer unit chain and the composition of the monomer unit, for example.

As mentioned above, compositions for use in preparing assay reagents or for use as assay reagents comprise a solid support and a coating of a synthetic copolymer. The synthetic copolymer comprises two or three monomers that are copolymerized to form the polymer. The synthetic copolymer comprises a polymer backbone with pendant moieties, the nature of which are related directly to the nature of the copolymerized monomers. In some embodiments the copolymer comprises a polyethylenic backbone, which comprises a linear chain of ethylenic groups, i.e., —(CHR—CHR)— groups (where R is alkyl or hydrogen) formed from monomers comprising double bonds. Other types of polymer backbones are also included and depend on the nature of the monomers. In some examples, the polyethylenic backbone has the formula —$CH_2$—$CHR^9$— wherein $R^9$ is H or alkyl of from 1 to 6 carbon atoms, or 1 to 5 carbon atoms, or 1 to 4 carbon atoms, or 1 to 3 carbon atoms, or 1 to 2 carbon atoms, or 2 to 5 carbon atoms, or 2 to 4 carbon atoms, or 2 to 3 carbon atoms, 3 to 5 carbon atoms, or 3 to 4 carbon atoms, or 4 to 5 carbon atoms, or 1 carbon atom.

The first copolymerized monomer comprises a pendant moiety of the formula:

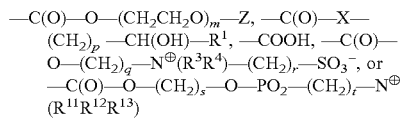

wherein:

$R^1$ is H or alkyl of from 1 to 6 carbon atoms, or 1 to 5 carbon atoms, or 1 to 4 carbon atoms, or 1 to 3 carbon atoms, or 1 to 2 carbon atoms, or 2 to 5 carbon atoms, or 2 to 4 carbon atoms, or 2 to 3 carbon atoms, 3 to 5 carbon atoms, or 3 to 4 carbon atoms, or 4 to 5 carbon atoms, or 1 carbon atom;

X is O or $NR^2$ wherein $R^2$ is H or alkyl of from 1 to 6 carbon atoms, or 1 to 5 carbon atoms, or 1 to 4 carbon atoms, or 1 to 3 carbon atoms, or 1 to 2 carbon atoms, or 2 to 5 carbon atoms, or 2 to 4 carbon atoms, or 2 to 3 carbon atoms, 3 to 5 carbon atoms, or 3 to 4 carbon atoms, or 4 to 5 carbon atoms, or 1 carbon atom;

Z is H or alkyl of from 1 to 6 carbon atoms, or 1 to 5 carbon atoms, or 1 to 4 carbon atoms, or 1 to 3 carbon atoms, or 1 to 2 carbon atoms, or 2 to 5 carbon atoms, or 2 to 4 carbon atoms, or 2 to 3 carbon atoms, 3 to 5 carbon atoms, or 3 to 4 carbon atoms, or 4 to 5 carbon atoms, or 1 carbon atom;

m is 1 to 100, or 2 to 100, or 3 to 100, or 4 to 100, or 1 to 90, or 1 to 80, or 1 to 70, or 1 to 60, or 1 to 50, 1 to 40, or 1 to 30, or 1 to 20, or 1 to 10, or 1 to 5, or 5 to 100, or 5 to 90, or 5 to 80, or 5 to 70, or 5 to 60, or 5 to 50, 5 to 40, or 5 to 30, or 5 to 20, or 5 to 10, or 10 to 100, or 10 to 90, or 10 to 80, or 10 to 70, or 10 to 60, or 10 to 50, or 10 to 40, or 10 to 30, or 20 to 30, or 10 to 20, for example;

$R^3$ and $R^4$ are independently H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, or 1 carbon atom, for example;

$R^{11}$, $R^{12}$ and $R^{13}$ are independently H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, or 1 carbon atom, for example;

p is to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example;

q is 10, or 1 to 9, or 1 to 8, or 1 to 7, or 1 to 6, or 1 to 5, 1 to 4, or to 3, or to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example;

r is 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example;

s is 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example;

t is to 10, or 1 to 9, or 1 to 8, or 1 to 7, or 1 to 6, or 1 to 5, 1 to 4, or to 3, or to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example.

The second copolymerized monomer comprises a pendant moiety of the formula:

A is O or NR wherein R is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, or 1 carbon atom, for example;

n is 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example; and G is CHO; $CH(OR^8)_2$ wherein $R^8$ is alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, or 1 carbon atom, for example; COOH or a derivative thereof; OH; or an sbp member; or

wherein R is as defined above and J is an sbp member.

The third copolymerized monomer comprises a pendant moiety of the formula: —COOH or a derivative thereof. The derivative may be, by way of illustration and not limitation, an ester, an amide, a carbamate, or a hydrazide, for example. In some examples, the third copolymerized monomer comprises a pendant moiety of the formula: —$COOR^{10}$ wherein $R^{10}$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example As mentioned above, when the first copolymerized monomer is —C(O)—X—$(CH_2)_p$—CH(OH)—$R^1$ wherein $R^1$ is other than H, the synthetic copolymer comprises all three of the first copolymerized monomer, the second copolymerized monomer and the third copolymerized monomer.

Examples of synthetic copolymers in accordance with the principles described herein may be synthesized according to standard polymer chemistry for the synthesis of random copolymers using appropriate monomeric units as identified above. In some embodiments, monomer units comprising one or more polymerizable functionalities may be combined in a single polymerization step. In this latter polymerization approach, the number of each of the copolymerized monomers of the copolymer may be controlled by controlling the molar concentration of the monomer units. For example, the number of copolymerized monomers may be controlled by the feed ratio of the monomers during polymerization. Accordingly, during a polymerization the feed ratio of one of the monomers may be increased over that of the other monomers. The ratio of the copolymerizable monomers (first, second and third copolymerizable monomers) during a polymerization may be 1:1:0, 1:1:1, or 1.5:1:0, or 1.5:1:1, or 2:1:0, or 2:1:1, or 2.5:1:0, or 2.5:1:1, or 3:1:0, or 3:1:1, or 3.5:1:0, or 3.5:1:1, or 4:1:0, or 4:1:1, or 4.5:1:0, or 4.5:1:1, or 5:1:0, or 5:1:1, or 5.5:1:0, or 5.5:1:1, or 6:1:0, or 6:1:1, 10:1:0, 0:10:1, 100:1:0, 0:1:100, for example. This feed ratio controls the value of x, y and z in the formulas herein.

The random copolymers may be prepared by any polymerization technique for the preparation of random copolymers. Polymerization techniques include, for example, radical polymerization, atom transfer radical polymerization, reversible addition fragmentation and chain transfer polymerization, nitroxide mediated polymerization, and so forth. The conditions for the polymerization such as, for example, temperature, reaction medium, pH, duration, and the order of addition of the reagents are dependent on one or more of the type of polymerization employed, the nature of the monomer reagents including any polymerizable functionality employed and the nature of any catalyst employed, for example. Such conditions are generally known since the types of polymerization techniques that can be used are well-known in the art.

The number of carbon atoms in the chain of the backbone of the copolymer is dependent on the number and nature of each of the copolymerized monomer units such as, e.g., the number of carbon atoms in the polymerizable functionality of the monomer units, and the weight average molecular weight of the copolymer, for example. The number of each of the first copolymerized monomer, the second copolymerized monomer and the third copolymerized monomer (if present), respectively, in the copolymer is 1 to about 1,000, or 1 to about 750, or 1 to about 500, or 1 to about 250, or 1 to about 100, or 1 to about 50, or 2 to about 1,000, or 2 to about 750, or 2 to about 500, or 2 to about 250, or 2 to about 100, or 2 to about 50, or 5 to about 1,000, or 5 to about 750, or 5 to about 500, or 5 to about 250, or 5 to about 100, or 5 to about 50, or 10 to about 1,000, or 10 to about 750, or 10 to about 500, or 10 to about 250, or 10 to about 100, or 10 to about 50, or 100 to about 1,000, or 100 to about 750, or 100 to about 500, or 100 to about 250, for example.

The term "polymerizable functionality" refers to a portion of a monomer unit that reacts with a portion of another molecule of the monomer or a portion of a molecule of a different monomer such as, for example, a moiety that comprises one or more double or triple bonds such as, for example, allyl groups, vinyl groups, acrylate groups, methacrylate groups, acrylamide groups and methacrylamide groups In some embodiments the weight average molecular weight (daltons) (Da) of the copolymer is about 300 to about 10,000,000 or more, or about 500 to about 10,000,000, or about 1,000 to about 10,000,000, or about 10,000 to about 10,000,000, or about 100,000 to about 10,000,000, or 300 to about 5,000,000 or more, or about 500 to about 5,000,000, or about 1,000 to about 5,000,000, or about 10,000 to about 5,000,000, or about 100,000 to about 5,000,000, or 300 to about 1,000,000 or more, or about 500 to about 1,000,000, or about 1,000 to about 1,000,000, or about 10,000 to about 1,000,000, or about 100,000 to about 1,000,000, or about 100 to about 750,000, or about 500 to about 750,000, or about 1,000 to about 750,000, or about 10,000 to about 750,000, or about 100,000 to about 750,000, or about 100 to about 500,000, or about 200 to about 500,000, or about 1,000 to about 500,000, or about 10,000 to about 500,000, or about 100,000 to about 500,000, for example.

In some examples, a synthetic copolymer in accordance with the principles described herein may be employed as a coating on a paramagnetic solid support. The term "paramagnetic" refers to substances in which slight magnetic properties may be introduced resulting in a weak attraction to either pole of a magnet, a state that is lost upon removal from the magnetic field. Paramagnetic substances typically have unpaired "d" electrons. Paramagnetic substances include, but are not limited to, metal salts such as, for example, metal oxides, and metal halides, for example; and metallic elements, for example. The metal may be, by way of illustration and not limitation, iron, chromium, lithium, sodium, magnesium, aluminum, manganese, strontium, zirconium, molybdenum, ruthenium, rhodium, palladium, tin, samarium, europium, tungsten, and platinum, for example.

The paramagnetic solid support can have any of a number of shapes such as, for example, particulate, including beads and particles, film, membrane, tube, well, strip, rod, and planar surfaces such as, e.g., plates. Depending on the type of assay, the solid support may or may not be suspendable in the medium in which it is employed.

In some embodiments the paramagnetic solid support is a paramagnetic particle. The particles generally have an average diameter of about 0.02 to about 100 microns, or about 0.05 to about 100 microns, or about 0.1 to about 100 microns, or about 0.5 to about 100 microns, or about 0.02 to about 50 microns, or about 0.05 to about 50 microns, or about 0.1 to about 50 microns, or about 0.5 to about 50 microns, or about 0.02 to about 20 microns, or about 0.05 to about 20 microns, or about 0.1 to about 20 microns, or about 0.5 to about 20 microns, for example. In some embodiments, the particles have an average diameter from about 0.05 microns to about 20 microns or from about 0.3 microns to about 10 microns, or about 0.3 microns to about 5 microns, for example. In some embodiments, by way of illustration and not limitation, the paramagnetic particles are iron (II) oxide particles, iron (III) oxide particles, mixtures of iron (II) oxide and iron (III) oxide particles, chromium oxide particles, and particles formed from oxides of lithium, sodium, magnesium, aluminum, manganese, strontium, zirconium, molybdenum, ruthenium, rhodium, palladium, tin, samarium, europium, tungsten, or platinum, and mixtures of two or more of the above, for example.

As mentioned above, a synthetic copolymer in accordance with the principles described herein may be employed as a coating on a paramagnetic solid support. Coating the support with the copolymer may be accomplished in a number of ways. The copolymer may be attached to the surface of the support covalently. In some embodiments, covalent attachment may be carried out by reaction of some of the reactive functionalities such as, for example, aldehyde groups, of the copolymer with a functionality on the surface of the support. As mentioned above, in some embodiments, depending on the nature of the support, suitable reactive functionalities may be already present on the surface of the support or they may be synthetically introduced on the surface. The remaining reactive functionalities such as, for example, aldehyde groups, are available for reaction with a suitably functionalized sbp member, for example.

The term "reactive functionality" is a functionality that can react with a corresponding reactive functionality on another molecule to form a covalent bond. Such reactive functionalities include, by way of illustration and not limitation, aldehyde, carboxy, amino, imino, sulfhydryl and hydroxy, for example. In some embodiments the reactive functionality is an aldehyde and the first copolymerized monomer comprises an aldehyde moiety.

The term "derivative of a reactive functionality" means a moiety that is formed by the reaction of a reactive functionality with another moiety that comprises a functionality reactive with the reactive functionality thereby forming a covalent bond linking two molecules together to form the derivative. The derivative of a reactive functionality may comprise an acetal, a carboxy ester, an amide, an ether or a thioether, for example. In some embodiments the derivative of a reactive functionality may be a reaction product of a reactive functionality with a reactive functionality of an sbp member whereby the sbp member becomes covalently bound to the copolymer. Functionalities on the sbp member may be present naturally on the sbp member or may be introduced synthetically into the sbp member. Such functionalities include, for example, amine groups, hydroxyl groups, sulfhydryl groups and carboxyl groups. In some embodiments the derivative of a reactive functionality may be a reaction product of a reactive functionality with a reactive functionality of a particle whereby the copolymer becomes covalently bound to the particle thereby providing a coating of the copolymer on the surface of the particle. Functionalities on the particle may be present naturally on the particle or may be introduced synthetically on the surface of the particle. Such functionalities include amine groups, hydroxyl groups, azide groups and carboxyl groups, for example. In some embodiments the derivative of a reactive functionality is an aldehyde derivative.

The term "aldehyde derivative" means a moiety that is formed by the reaction of an aldehyde group with another moiety that comprises a functionality reactive with an aldehyde group. The aldehyde derivative may be an acetal that results from the reaction of two alcohol functionalities with a carbonyl oxygen of an aldehyde. The aldehyde derivative may be a reaction product of an aldehyde group with an sbp member by means of reaction of the aldehyde with a functionality of the sbp member. Functionalities on the sbp member may be present naturally on the sbp member or may be introduced synthetically into the sbp member. Such functionalities include, for example, amine groups. The reaction between an aldehyde group and an sbp member may be by means of, for example, Schiff's base formation between an alkyl amine or an aryl amine of the sbp member and the aldehyde group. The reaction may be by means of reductive amination involving the aldehyde group and an amine group of the sbp member. In other embodiments, the aldehyde derivatives include, for example, acetals and bisulphite addition compounds. In some embodiments the aldehyde functionality may react with a corresponding amine group on the surface of a particle whereby the particle becomes covalently bound to the copolymer thereby providing a coating of the copolymer on the surface of the particle. Functionalities on the particle may be present naturally on the particle or may be introduced synthetically on the surface of the particle.

In some embodiments, the amount of the synthetic copolymer coated on the paramagnetic solid support is dependent on one or more of the nature of the support, the nature of the copolymer, the nature of an sbp member, whether attachment of the copolymer to the support is by virtue of the aldehyde bearing site, and whether an sbp member is attached to the aldehyde bearing site, for example. In some embodiments the amount (percent by weight) of copolymer coated on the support is about 0.1 to about 10%, or about 0.1 to about 9%, or about 0.1 to about 8%, or about 0.1 to about 7%, or about 0.1 to about 6%, or about 0.1 to about 5%, or about 0.1 to about 4%, or about 0.1 to about 3%, or about 0.1 to about 2%, or about 0.1 to about 1%, or about 0.1 to about 0.5%, or about 1 to about 10%, or about 1 to about 9%, or about 1 to about 8%, or about 1 to about 7%, or about 1 to about 6%, or about 1 to about 5%, or about 1 to about 4%, or about 1 to about 3%, or about 1 to about 2%, or about 0.05 to about 0.5%, or about 0.06 to about 0.5%, or about 0.07 to about 0.5%, or about 0.08 to about 0.5%, or about 0.09 to about 0.5%, or about 0.1 to about 0.5%, or about 0.05 to about 0.4%, or about 0.06 to about 0.4%, or about 0.07 to about 0.4%, or about 0.08 to about 0.4%, or about 0.09 to about 0.4%, or about 0.1 to about 0.4%, or about 0.05 to about 0.3%, or about 0.06 to about 0.3%, or about 0.07 to about 0.3%, or about 0.08 to about 0.3%, or about 0.09 to about 0.3%, or about 0.1 to about 0.3%, or about 0.05 to about 0.2%, or about 0.06 to about 0.2%, or about 0.07 to about 0.2%, or about 0.08 to about 0.2%, or about 0.09 to about 0.2%, or about 0.1 to about 0.2%, for example.

The selection of a copolymer coating for a paramagnetic solid support depends on one or more of a number of factors such as, for example, the type of assay in which the paramagnetic solid support is employed, the expected concentration range of an analyte, the physical characteristics and origin of an sbp member such as an antibody used in an assay, the variation in effective sbp member coating density, the pH of the final reaction mixture, and the ionic strength of the final reaction mixture. Depending on such factors, one copolymer coating may be preferred over another copolymer coating in any particular application.

As indicated above, a composition for use as an assay reagent in accordance with the principles described herein may comprise an sbp member, which is one of two different molecules, having an area on the surface or in a cavity, which specifically binds to and is thereby defined as complementary with a particular spatial and polar organization of the other molecule. The sbp members will usually be members of an immunological pair such as antigen-antibody or hapten-antibody although other specific binding pairs such as biotin-avidin, hormones-hormone receptors, enzyme-substrate, nucleic acid duplexes, IgG-protein A, polynucleotide pairs such as DNA-DNA, DNA-RNA, for example, are not immunological pairs but are included within the scope of the phrase sbp member. In some embodiments, depending on the nature of the assay to be conducted as explained more fully below, other reagents are included in the medium such as, for example, other sbp members and members of a signal producing system ("sps member(s)").

The term "hapten" refers to a compound capable of binding specifically to corresponding antibodies, but does not itself act as an immunogen (or antigen) for preparation of the antibodies. Haptens have a molecular weight less than about 5,000, or less than about 4,000, or less than about 3,000, or less than about 2,000, or less than about 1,500, for example. The term "antigen" refers to compounds that are immunogenic and lead to the formation of antibodies upon administration to a host. Antigens have a molecular weight more than about 5,000, or more than about 10,000, for example.

The sbp member is associated with the paramagnetic solid support of a composition in accordance with the principles described herein. As used herein, the phrase "associated with" includes covalent binding of one moiety to another moiety either by a direct bond or through a spacer group, non-covalent binding of one moiety to another moiety either directly or by means of specific binding pair members bound to the moieties, and coating one moiety on another moiety, for example. In some examples the sbp member is directly associated or bound to the paramagnetic solid support by means of covalent linking to the copolymer coated on the paramagnetic solid support. In some examples the copolymer is covalently linked to an aldehyde-bearing site of the copolymer coating the paramagnetic solid support.

In some examples, the sbp member is associated or bound to the paramagnetic solid support indirectly by means of the binding of a small molecule to a binding partner for the small molecule. The small molecule is an organic molecule that has a molecular weight in the range of about 100 to about 2,000, or about 100 to about 1,500, or about 100 to about 1,000, or about 100 to about 500, or about 100 to about 400, or about 100 to about 300, or about 100 to about 200, or about 200 to about 2,000, or about 200 to about 1,500, or about 200 to about 1,000, or about 200 to about 500, or about 200 to about 400, or about 200 to about 300, for example. Examples of small molecule-binding partner for the small molecule pairs, by way of illustration and not limitation, include biotin-binding partner for biotin (e.g., avidin, streptavidin, or antibody for biotin), desthiobiotin-binding partner for desthiobiotin (e.g., avidin, streptavidin, or antibody for desthiobiotin), digoxin-binding partner for digoxin (e.g., antibody for digoxin, etc.), fluorescein-binding partner for fluorescein (antibody for fluorescein, etc.), rhodamine-binding partner for rhodamine (e.g., antibody for rhodamine), and peptide-binding partner for the peptide (antibody for the peptide, etc.), for example. The phrase "binding partner" refers to a molecule that is an sbp member.

Examples of Copolymers

The following examples of copolymers that may be employed as coatings of paramagnetic solid supports in accordance with the principles described herein are by way of illustration and not limitation.

In some embodiments a copolymer has the formula:

$$\left[\begin{array}{c}R^7\\|\\\text{—}\end{array}\right]_z\left[\begin{array}{c}R^5\\|\\\text{—}\\|\\D^1\end{array}\right]_x\left[\begin{array}{c}R^6\\|\\\text{—}\\|\\D^2\end{array}\right]_y$$

wherein:
D$^1$ is —C(O)—O—(CH$_2$CH$_2$O)$_m$—Z, —C(O)—X—(CH$_2$)$_p$—CH(OH)—R$^1$, —COOH or a derivative thereof, —C(O)—O—(CH$_2$)$_q$—N$^\oplus$(R$^3$R$^4$)—(CH$_2$)$_r$—SO$_3^-$, or —C(O)—O—(CH$_2$)$_s$—O—PO$_2$—(CH$_2$)$_t$—N$^\oplus$(R$^{11}$R$^{12}$R$^{13}$)
wherein:
X is O or NR$^2$ wherein R$^2$ is H or alkyl of from 1 to 6 carbon atoms and variants set forth above,
Z is H or alkyl of from 1 to 6 carbon atoms and variants set forth above, R$^1$ is H or alkyl of from 1 to 6 carbon atoms and variants set forth above,
m is 1 to 100 and variants set forth above,
R$^3$ and R$^4$ are independently H or alkyl of from 1 to 6 carbon atoms and variants set forth above,
R$^{11}$, R$^{12}$ and R$^{13}$ are independently H or alkyl of from 1 to 6 carbon atoms and variants as set forth above,
p is 1 to 10 and variants set forth above,
q is 1 to 10 and variants set forth above,
r is 1 to 10 and variants set forth above,
s is 1 to 10 and variants set forth above,
t is 1 to 10 and variants set forth above, and D$^2$ is (a) —C(O)-A-(CH$_2$)$_n$-G wherein A is O or NR wherein R is H or alkyl of from 1 to 6 carbon atoms and variants set forth above, and n is 1 to 10 and wherein G is CHO; CH(OR$^8$)$_2$ wherein R$^8$ is alkyl of from 1 to 6 carbon atoms and variants set forth above; COOH or a derivative thereof and variants set forth above; OH; or a member of a specific binding pair; or (b) —OC(O)NR-J wherein R is as defined above and J is a member of a specific binding pair; all with and variants as set forth above;

D$^3$ is —COOH or a derivative thereof and variants set forth above;

R$^5$, R$^6$ and R$^7$ are independently H or alkyl of from 1 to 6 carbon atoms and variants set forth above;

x is 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example;

y is 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example; and z is 0 or 1 to about 1000 with the proviso that z is not 0 when D$^1$ is —C(O)—NH—(CH$_2$)$_p$—CH(OH)—R$^1$ wherein R$^1$ is other than H. When z is not 0, z may be 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example.

In some examples, the copolymer has the above formula wherein:
A is NR wherein R is H or alkyl of from 1 to 6 carbon atoms and variants set forth above;
n is 1 to 10;
G is CHO; CH(OR$^8$)$_2$ wherein R$^8$ is alkyl of from 1 to 6 carbon atoms and variants set forth above; or a member of a specific binding pair;
D$^1$ is —C(O)—O—(CH$_2$CH$_2$O)$_m$—Z, wherein Z is H or methyl and m is 1 to 100 and variants set forth above;
R$^5$ and R$^6$ are independently H or alkyl of from 1 to 6 carbon atoms and variants set forth above;
x is 1 to about 1000 and variants set forth above;

y is 1 to about 1000 and variants set forth above; and z is 0.

In some examples, the copolymer has the above formula wherein:

A is NR wherein R is H or alkyl of from 1 to 6 carbon atoms and variants set forth above;

n is 1 to 10 and variants set forth above;

G is CHO; CH(OR$^8$)$_2$ wherein R$^8$ is alkyl of from 1 to 6 carbon atoms and variants set forth above; or a member of a specific binding pair;

D$^1$ is —C(O)—O—(CH$_2$)$_q$—N$^\oplus$(R$^3$R$^4$)—(CH$_2$)$_r$—SO$_3^-$, wherein R$^3$ and R$^4$ are independently H or alkyl of from 1 to 6 carbon atoms and variants set forth above, q is 1 to 10 and variants set forth above and r is 1 to 10 and variants set forth above;

R$^5$ and R$^6$ are independently H or alkyl of from 1 to 6 carbon atoms and variants set forth above;

x is 1 to about 1000 and variants set forth above;

y is 1 to about 1000 and variants set forth above; and z is 0.

In some examples, the copolymer has the above formula wherein:

A is NR wherein R is H or alkyl of from 1 to 6 carbon atoms and variants set forth above;

n is 1 to 10 and variants set forth above;

G is CHO; CH(OR$^8$)$_2$ wherein R$^8$ is alkyl of from 1 to 6 carbon atoms and variants set forth above; or a member of a specific binding pair;

D$^1$ is —C(O)—O—(CH$_2$)$_s$—O—PO$_2$—(CH$_2$)$_t$—N$^\oplus$ (R$^{11}$R$^{12}$R$^{13}$), wherein s is 1 to 10 and variants set forth above and t is 1 to 10 and variants set forth above;

R$^{11}$, R$^{12}$ and R$^{13}$ are independently H or alkyl of from 1 to 6 carbon atoms and variants set forth above;

R$^5$ and R$^6$ are independently H or alkyl of from 1 to 6 carbon atoms and variants set forth above;

x is 1 to about 1000 and variants set forth above;

y is 1 to about 1000 and variants set forth above; and z is 0.

In some examples, the copolymer has the above formula wherein:

A is NR wherein R is H or alkyl of from 1 to 6 carbon atoms and variants set forth above;

n is 1 to 10 and variants set forth above;

G is CHO; CH(OR$^8$)$_2$ wherein R$^8$ is alkyl of from 1 to 6 carbon atoms and variants set forth above; or a member of a specific binding pair;

D$^1$ is —C(O)—X—(CH$_2$)$_p$—C(OH)—R$^1$, wherein R$^1$ is H or alkyl of from 1 to 6 carbon atoms and variants set forth above, X is NR$^2$ wherein R$^2$ is H or alkyl of from 1 to 6 carbon atoms and variants set forth above and p is 1 to 10 and variants set forth above, D$^3$ is —COOH or a derivative thereof and variants set forth above;

R$^5$, R$^6$ and R$^7$ are independently H or alkyl of from 1 to 6 carbon atoms and variants set forth above;

x is 1 to about 1000 and variants set forth above;

y is 1 to about 1000 and variants set forth above; and z is 1 to about 1000 and variants set forth above.

In some examples, the copolymer has the above formula wherein:

A is NR wherein R is H or alkyl of from 1 to 6 carbon atoms and variants set forth above;

n is 1 to 10 and variants set forth above;

G is CHO; CH(OR$^8$)$_2$ wherein R$^8$ is alkyl of from 1 to 6 carbon atoms and variants set forth above; or a member of a specific binding pair;

D$^1$ is —C(O)—X—(CH$_2$)$_p$—C(OH)—R$^1$, wherein R$^1$ is H or alkyl of from 1 to 6 carbon atoms and variants set forth above, p is 1 to 10 and variants set forth above, D$^3$ is —COOH or a derivative thereof and variants set forth above;

R$^5$, R$^6$ and R$^7$ are independently H or alkyl of from 1 to 6 carbon atoms and variants set forth above;

x is 1 to about 1000 and variants set forth above;

y is 1 to about 1000 and variants set forth above; and z is 1 to about 1000 and variants set forth above.

In some examples, the copolymer has the above formula wherein:

A is NH;

n is 1;

G is CHO;

D$^1$ is —COOH;

R$^5$ is H and R$^6$ is methyl;

x is 1 to about 1000 and variants set forth above;

y is 1 to about 1000 and variants set forth above; and z is 0.

In some examples, the copolymer has the above formula wherein:

A is NH;

n is 1;

G is CHO;

D$^1$ is —C(O)—O—(CH$_2$)—CH$_2$(OH);

R$^5$ is methyl and R$^6$ is methyl;

x is 1 to about 1000 and variants set forth above;

y is 1 to about 1000 and variants set forth above; and z is 0.

In some examples, the copolymer has the above formula wherein:

A is NH;

n is 1;

G is CHO;

D$^1$ is —C(O)—O—(CH$_2$)$_2$—N$^\oplus$(R$^3$R$^4$)—(CH$_2$)$_3$—SO$_3^-$;

R$^5$ is methyl and R$^6$ is methyl;

x is 1 to about 1000 and variants set forth above;

y is 1 to about 1000 and variants set forth above; and z is 0.

In some examples, the copolymer has the above formula wherein:

A is NH;

n is 1;

G is CHO;

D$^1$ is —C(O)—O—(CH$_2$)$_2$—O—PO$_2$—(CH$_2$)$_2$—N$^\oplus$(CH$_3$)$_3$;

R$^5$ is methyl and R$^6$ is methyl;

x is 1 to about 1000 and variants set forth above;

y is 1 to about 1000 and variants set forth above; and z is 0.

In some examples, the copolymer has the above formula wherein:

A is NH;

n is 1;

G is CHO;

D$^1$ is —C(O)—O—(CH$_2$CH$_2$O)$_m$—CH$_3$ wherein m is 6-8, 8-10 or 20-25;

R$^5$ is methyl and R$^6$ is methyl;

x is 1 to about 1000 and variants set forth above;

y is 1 to about 1000 and variants set forth above; and z is 0.

In some examples, the copolymer has the above formula wherein:

A is NH;

n is 1;

G is CHO;
D¹ is —C(O)—X—(CH$_2$)$_p$—CH$_2$(OH), p is 2,
D³ is —COOH;
R⁵ and R⁶ are methyl and R⁷ is H;
x is 1 to about 1000 and variants set forth above;
y is 1 to about 1000 and variants set forth above; and
is 1 to about 1000 and variants set forth above.

General Description of Assays in which the Present Compositions May be Utilized

The following discussion is by way of illustration and not limitation. The present compositions may be employed in any assay that involves magnetic separation of one or more of any of the assay components or products. Since the assays involve one or more separation steps, they are referred to as heterogeneous assays. The assays can be competitive or non-competitive.

An assay is a method of determining in a sample one or both of the presence and the amount of an analyte in the sample. The analyte is a substance of interest or the compound or composition to be detected and/or quantitated. Analytes include, for example, drugs, metabolites, pesticides and pollutants. Representative analytes, by way of illustration and not limitation, include alkaloids, steroids, lactams, aminoalkylbenzenes, benzheterocyclics, purines, drugs derived from marijuana, hormones, polypeptides which includes proteins, immunosuppressants, vitamins, prostaglandins, tricyclic antidepressants, anti-neoplastics, nucleosides and nucleotides including polynucleosides and polynucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, and metabolites and derivatives of all of the above. Also included are metabolites related to disease states, aminoglycosides, such as gentamicin, kanamicin, tobramycin, and amikacin, and pesticides such as, for example, polyhalogenated biphenyls, phosphate esters, thiophosphates, carbamates and polyhalogenated sulfenamides and their metabolites and derivatives. The term "analyte" also includes combinations of two or more of polypeptides and proteins, polysaccharides and nucleic acids. Such combinations include, for example, components of bacteria, viruses, chromosomes, genes, mitochondria, nuclei and cell membranes. Protein analytes include, for example, immunoglobulins, cytokines, enzymes, hormones, cancer antigens, nutritional markers and tissue specific antigens. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, ca-fetoprotein, acid phosphatase, CA19.9, CA15.3 and CA125, tissue specific antigens, such as, e.g., alkaline phosphatase, myoglobin, CPK-MB and calcitonin, and peptide hormones. Other polymeric materials of interest are mucopolysaccharides and polysaccharides. As indicated above, the term analyte further includes oligonucleotide and polynucleotide analytes such as m-RNA, r-RNA, t-RNA, DNA and DNA-RNA duplexes, for example.

The sample to be tested may be non-biological or biological. "Non-biological samples" are those that do not relate to a biological material and include, for example, soil samples, water samples and mineral samples. The phrase "biological sample" refers to any biological material, such as, for example, body fluid and body tissue, which is obtained from the body of a mammal including humans, birds, reptiles, and other vertebrates. Body fluids include, for example, whole-blood, plasma, serum, interstitial fluid, sweat, saliva, urine, semen, blister fluid, inflammatory exudates, stool, sputum, cerebral spinal fluid, tears, mucus, lymphatic fluid, vaginal mucus, and the like. The biological tissue includes, but is not limited to, excised tissue from an organ or other body part of a host, e.g., tissue biopsies; hair and skin; for example.

In a method of determining an analyte in a sample, a combination is provided in a medium. The combination comprises the sample, an sps member that is bound to an sbp member that binds to the analyte or binds to an analyte analog, and a composition comprising a paramagnetic solid support that comprises an sbp member, which binds to the analyte or binds to an sbp member that binds to the analyte to form a complex related to the presence of the analyte, and a coating of a synthetic copolymer as described above.

An analyte analog is a modified analyte or an organic radical that can compete with an analyte for a receptor, the modification providing means to join an analyte analog to another molecule. The analyte analog differs from the analyte by at least replacement of a hydrogen with a bond that links the analyte analog to another moiety. The analyte analog can bind to a receptor in a manner similar to the analyte. The analog could be, for example, an antibody directed against the idiotype of an antibody to the analyte or an analyte that has been modified to incorporate an sps member.

The sample can be prepared in any convenient medium. For example, the sample may be prepared in an assay medium, which is discussed more fully hereinbelow. In some instances a pretreatment may be applied to the sample such as, for example, to lyse blood cells or to release an analyte from endogenous binding substances in the sample. Such pretreatment is usually performed in a medium that does not interfere subsequently with an assay. An aqueous medium is preferred for the pretreatment where the aqueous medium may be solely water or solely an organic solvent or mixtures thereof.

An assay medium, which in some embodiments is an aqueous buffered medium at a moderate pH, is generally one that provides optimum assay sensitivity. The aqueous medium may be solely water or may include from 0.1 to about 40 volume percent of a cosolvent such as, for example, a water miscible organic solvent, e.g., an alcohol, an ether or an amide. The pH for the medium will usually be in the range of about 4 to about 11, or in the range of about 5 to about 10, or in the range of about 6.5 to about 9.5, for example. The pH utilized is often the result of a compromise between optimum binding of the binding members of any specific binding pairs and the pH optimum for other reagents of the assay such as members of the signal producing system, for example. Various buffers may be used to achieve the desired pH and maintain the pH during the determination. Illustrative buffers include borate, phosphate, carbonate, tris, barbital, PIPES, HEPES, MES, ACES, MOPS, BICINE, and the like. The particular buffer employed is not critical, but in an individual assay one or another buffer may be preferred.

Various ancillary materials may be employed in the assay methods. For example, in addition to buffers, the medium may comprise stabilizers for the medium and for the reagents employed. In some embodiments, in addition to these additives, the medium may include proteins such as, e.g., albumins; organic solvents such as, e.g., formamide; quaternary ammonium salts; polyanions such as, e.g., dextran sulfate; binding enhancers, e.g., polyalkylene glycols; polysaccharides such as, e.g., dextran, trehalose, or the like. The medium may also comprise agents for preventing the formation of blood clots. Such agents are well known in the art and include, for example, EDTA, EGTA, citrate and heparin. The medium may also comprise one or more preservatives as are known in the art such as, for example, sodium azide, neomycin sulfate, PROCLIN® 300 and Streptomycin. Any of the above materials, if employed, is present in a concentration or amount sufficient to achieve the desired effect or function.

As mentioned above, for an assay for an analyte the paramagnetic solid support comprises an sbp member, which binds specifically to the analyte or binds specifically to an sbp member that binds specifically to the analyte, to form a complex related to the presence of the analyte. The nature of the sbp member on the paramagnetic solid support depends on one or more of the nature of the analyte, the nature of the assay employed, and conditions under which an assay is performed, for example. In an example, the sbp member on the paramagnetic solid support may be an antibody that binds specifically to the analyte. In another example, the sbp member on the paramagnetic solid support may be an analyte analog that binds to an antibody for the analyte. In another example, the sbp member on the paramagnetic solid support may be an antibody that binds specifically to another antibody that binds specifically to the analyte. In another example, the sbp member on the paramagnetic solid support may be a member of an sbp that is specific for a moiety other than an analyte analog or an antibody for the analyte, such as, a binding partner for a small molecule, where the complementary sbp member is a binding partner for the small molecule such as, but not limited to, streptavidin (for biotin), avidin (for biotin), and folate binding protein (for folate), for example.

In addition to the above, the combination in the assay medium also comprises an sps member that is bound to an sbp member that specifically binds to the analyte or further comprises an sps member that is bound to an analyte analog. The nature of the molecule to which the sps member is bound depends on one or more of the nature of the analyte, the nature of the assay employed, and the nature of the sbp member on the paramagnetic solid support, for example. In an example, the sps member is bound to an antibody that specifically binds to the analyte. In another example, the sps member is bound to an analyte analog.

In the assay methods in accordance with the principles described herein, the above combination is subjected to conditions for forming the complex. Such conditions may include one or more incubation periods that may be applied to the medium at one or more intervals including any intervals between additions of various reagents employed in an assay including those mentioned above, some or all of which may be in the initial combination. The medium is usually incubated at a temperature and for a time sufficient for binding of various components of the reagents and binding between complementary sbp members such as, for example, an analyte and a complementary sbp member or first and second sbp members to occur. Moderate temperatures are normally employed for carrying out the method and usually constant temperature, preferably, room temperature, during the period of the measurement. In some embodiments incubation temperatures range from about 5° to about 99° C., or from about 15° C. to about 70° C., or from about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents, which is determined by one or more of the association rate constant, the concentration, the binding constant and dissociation rate constant, for example.

Following the above incubation periods, if any, the sps member is activated and the amount of the complex is detected. In some examples, the paramagnetic support to which the complex is bound is separated from the assay medium and optionally washed prior to activation of the sps member on the paramagnetic solid support. In some examples, the assay medium, from which the paramagnetic solid support is separated, is examined by activating complex not bound to the paramagnetic solid support. The amount of the complex is related to one or both of the presence and the amount of analyte in the sample. The detection of the complex is dependent on one or more of the nature of the assay being performed, the nature of the sps members, and the nature of the sbp members, for example.

As mentioned above, the composition also comprises an sps member. The nature of the sps member depends on the type of assay in which embodiments of the present compositions may be employed. The sps member may be a label, which is part of a signal producing system. The nature of the label is dependent on the particular assay format as discussed above. A signal producing system may include one or more components, at least one component being a detectable label, which generates a detectable signal that relates to one or both of the amount of bound and unbound label, i.e. the amount of label bound or not bound to analyte being detected or to an agent that reflects the amount of the analyte to be detected. The label is any molecule that produces or can be induced to produce a signal, and may be, but is not limited to, a fluorescer, a radiolabel, an enzyme, a chemiluminescent compound, or a sensitizer (including photosensitizers), for example. Thus, the signal is detected and/or measured by detecting enzyme activity, luminescence, light absorbance or radioactivity, for example, depending on the nature of the label.

Suitable labels include, by way of illustration and not limitation, chemiluminescent compounds such as acridinium esters (including acridinium esters comprising one or more substituents such as, but not limited to, hexaethylene glycol, isopropyloxy, and N-sulfopropyl, for example), luminol, and isoluminol, for example; enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; sensitizers including photosensitizers; coenzymes; enzyme substrates; radiolabels such as $^{125}I$, $^{131}I$, $^{14}C$, $^{3}H$, $^{57}Co$ and $^{75}Se$; for example.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include, for example, substrates, coenzymes, enhancers, additional enzymes, substances that react with enzymic products, catalysts, activators, cofactors, inhibitors, scavengers, metal ions, oxidizers, acids, bases, surfactants, and a specific binding substance required for binding of signal generating substances.

In some examples, a chemiluminescent compound is employed as an sps member. A chemiluminescent compound (chemiluminescer) is a compound that is chemically activatable and, as a result of such activation, emits light at a certain wavelength. Examples of chemiluminescers, by way of illustration and not limitation, include acridinium esters, olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as luminol; and aromatic compounds that can form endoperoxides, for example. As a consequence of the activation reaction, the chemiluminescers directly or indirectly cause the emission of light.

In some examples, the assay method is an immunoassay, which may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassay, inhibition immunoassays, induced luminescence assays, and fluorescent oxygen channeling assays, for example.

One general group of immunoassays in which embodiments of the present compositions may be employed to determine the presence and/or amount of an analyte in a sample includes immunoassays using a limited concentration of one of the assay reagents. Another group of immunoassays involves the use of an excess of one or more of the principal reagents.

In a typical competitive heterogeneous assay, an example of a composition in accordance with the principles described herein that comprises an sbp member that binds specifically to an analyte (e.g., an antibody for the analyte) is contacted with a medium containing the sample suspected of containing the analyte and the analyte conjugated to a label (labeled analyte analog). Analyte from the sample and labeled analyte analog compete for binding to the sbp member of the present composition. After magnetic separation of the composition in accordance with the principles described herein from the assay medium, the composition is examined for the amount of label bound to it. Activation of the label on the present composition produces a signal from the label, which is determined by conventional techniques. The amount of the signal from the label is inversely proportional to the amount of analyte in the sample because the labeled analyte analog competes with analyte from the sample for binding to the sbp member. That is, the more the amount of analyte in the sample, the less is the amount of labeled analyte analog that becomes bound to the present composition and the less is the amount of signal observed.

In a typical non-competitive sandwich assay, an immune sandwich complex is formed in an assay medium. The complex comprises the analyte, an sbp member (first sbp member) of the present compositions that binds to the analyte and a second sbp member that binds to the analyte. Subsequently, the immune sandwich complex is detected and is related to the amount of analyte in the sample. The immune sandwich complex is detected by virtue of the presence in the complex of a label of the second sbp member.

Some known assays utilize a signal producing system that employs first and second sps members. The sps members may be related in that activation of one member of the sps produces a product such as, e.g., light, which results in activation of another member of the sps.

In one approach in a sandwich assay, a first incubation of the present composition is contacted with a medium containing a sample suspected of containing the analyte. After a wash and separation step, the support of the present composition is contacted with a medium containing a second sbp member such as, for example, an antibody for the analyte, which contains a label such as a chemiluminescent compound or an enzyme, for a second incubation period. The labels are related in that activation of one of the labels activates the other label if the analyte is present in the medium. The support is again washed and separated from the medium and either the medium or the support is examined for the presence of a signal. The presence and amount of signal is related to the presence or amount of the analyte.

In some embodiments of known assays, the sps members comprise a sensitizer such as, for example, a photosensitizer, and a chemiluminescent composition where activation of the sensitizer results in a product that activates the chemiluminescent composition. The second sps member usually generates a detectable signal that relates to the amount of bound and/or unbound sps member, i.e. the amount of sps member bound or not bound to the analyte being detected or to an agent that reflects the amount of the analyte to be detected. In accordance with embodiments of the present invention, the present composition may comprise one of either the sensitizer reagent or the chemiluminescent reagent.

The concentration of the analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of the analyte present in the sample), the particular detection technique and the expected concentration of the analyte normally determine the concentrations of the various reagents.

The concentrations of the various reagents in the assay medium will generally be determined by the concentration range of interest of the analyte and the nature of the assay, for example. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of the analytes, for example, determine the concentrations of the various reagents.

As mentioned above, the sample and reagents are provided in combination in the medium. While the order of addition to the medium may be varied, there will be certain preferences for some embodiments of the assay formats described herein. The simplest order of addition is to add all the materials simultaneously and determine the effect that the assay medium has on the signal as in a homogeneous assay or separate a composition in accordance with the principles described herein by application of a magnetic field and examine the composition for the presence and/or amount of signal as in a heterogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

In an embodiment, the present invention is a method of determining in a sample one or more of the presence and amount of an analyte. A combination is provided in a medium. The combination comprises the sample and a composition comprising a particle comprising a member of a signal producing system, a member of the specific binding pair that binds to the analyte or to a second sbp member to form a complex related to the presence of the analyte and a coating of a copolymer. The copolymer has the formula:

$$\left[\begin{array}{c}R^7\\|\\\phantom{D^3}\\D^3\end{array}\right]_z\left[\begin{array}{c}R^5\\|\\\phantom{D^1}\\D^1\end{array}\right]_x\left[\begin{array}{c}R^6\\|\\\phantom{D^2}\\D^2\end{array}\right]_y$$

wherein:
  $D^1$ is —C(O)—O—(CH$_2$CH$_2$O)$_m$—Z, —C(O)—X—(CH$_2$)$_p$—CH(OH)—R$^1$, —COOH or a derivative thereof, —C(O)—O—(CH$_2$)$_q$—N$^\oplus$(R$^3$R$^4$)—(CH$_2$)$_r$—SO$_3^-$, or —C(O)—O—(CH$_2$)$_s$—O—PO$_2$—(CH$_2$)$_t$—N$^\oplus$(R$^{11}$R$^{12}$R$^{13}$),
  wherein:
    X is O or NR$^2$ wherein R$^1$ is H or alkyl of from 1 to 6 carbon atoms,
    Z is H or alkyl of from 1 to 6 carbon atoms,
    R$^2$ is H or alkyl of from 1 to 6 carbon atoms,
    m is 1 to 100,
    R$^3$ and R$^4$ are independently H or alkyl of from 1 to 6 carbon atoms,
    R$^{11}$, R$^{12}$ and R$^{13}$ are independently H or alkyl of from 1 to 6 carbon atoms,
    p is 1 to 10,
    q is 1 to 10,
    r is 1 to 10,
    s is 1 to 10,
    t is 1 to 10, and
  $D^2$ is —C(O)-A-(CH$_2$)$_n$-G wherein A is O or NR wherein R is H or alkyl of from 1 to 6 carbon atoms and n is 1 to 10 and wherein G is CHO; CH(OR$^8$)$_2$ wherein R$^8$ is alkyl of from 1 to 6 carbon atoms; COOH or a derivative thereof; OH; or a member of a specific binding pair;
  $D^3$ is —COOH or a derivative thereof;
  R$^5$, R$^6$ and R$^7$ are independently H or alkyl of from 1 to 6 carbon atoms;
  x is 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example;
  y is 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example; and
  z is 0 or 1 to about 1000 with the proviso that z is not 0 when $D^1$ is —C(O)—NH—(CH$_2$)$_p$—CH(OH)—R$^1$ wherein R$^1$ is other than H. When z is not 0, z may be 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example.

Particular Assay Methods Utilizing Examples of the Present Compositions

As mentioned above, compositions in accordance with the principles described herein may be employed in assays that utilize paramagnetic particles. One particular example of such an assay is an acridinium ester label immunoassay using paramagnetic particles as a solid phase ("ADVIA" immunoassay).

In one example of an ADVIA immunoassay, a detection system is employed that includes a small molecule-labeled analyte analog (capture moiety), an sbp member for the small molecule bound to copolymer-coated paramagnetic iron oxide particles in accordance with the principles described herein as a solid phase (SP), and an acridinium ester labeled antibody specific for the analyte (detection antibody). The small molecule may be, for example, biotin or fluorescein and the respective sbp member for the small molecule may be streptavidin or antibody for fluorescein. Analyte in a patient sample competes with labeled analyte analog of the capture moiety for binding to the acridinium ester labeled detection anti-analyte antibody. The assay may be carried out on a CENTAUR®, CENTAUR® XP or CENTAUR® CP apparatus (Siemens Healthcare Diagnostics Inc., Newark Del.) in accordance with the manufacturer's directions supplied therewith. After an appropriate incubation period, the paramagnetic particles are separated from the assay medium by application of a magnetic field. The paramagnetic particles are examined for the amount of signal from the acridinium ester labeled anti-analyte antibody by exposing the paramagnetic particles to an activation agent for the acridinium ester such as, for example, one or more of an acid, an oxidizer, a base and a surfactant.

In another example of an ADVIA immunoassay, the detection system employed for this example of an assay includes a small molecule-labeled antibody for an analyte (capture antibody), sbp member for the small molecule bound to copolymer-coated paramagnetic iron oxide particles in accordance with the principles described herein as a solid phase (SP), and an acridinium ester labeled analyte analog (detection hapten). Analyte in a patient sample competes with the acridinium ester labeled detection hapten for binding with anti-analyte antibody that is bound to the paramagnetic particles by virtue of the binding between the small molecule and the sbp member for the small molecule. The assay may be carried out on a CENTAUR®, CENTAUR® XP or CENTAUR® CP apparatus (Siemens Healthcare Diagnostics Inc., Newark Del.) in accordance with the manufacturer's directions supplied therewith. After an appropriate incubation period, the paramagnetic particles are separated from the assay medium by application of a magnetic field. The paramagnetic particles are examined for the amount of signal from the acridinium ester labeled analyte analog by exposing the paramagnetic particles to an activation agent for the acridinium ester.

As mentioned above, depending on the nature of the assay employed, the medium may further comprise one or more components such as, for example, a small molecule, an additional particle, an additional sps members and additional binding agents such as one or more sbp members (e.g., antibodies), which are different from those that are part of the present composition. Furthermore, again depending on the nature of the assay employed, other reagents may also be included in the initial combination or added subsequently.

Examination Step

In a next step of an assay method, the medium is examined for the presence of a complex comprising the analyte. One or both of the presence and amount of the complex indicates one or both of the presence and amount of the analyte in the sample.

The phrase "measuring the amount of analyte" refers to the quantitative, semiquantitative and qualitative determination of the analyte. Methods that are quantitative, semiquantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of assays in which the present compositions may be utilized. The terms "detecting" and "determining," as well as other common synonyms for measuring, are contemplated within the scope of assay methods.

In many embodiments the examination of the medium involves detection of a signal from the medium. One or both of the presence and amount of the signal is related to one or both of the presence and amount of the analyte in the sample. The particular mode of detection depends on the nature of the signal producing system. As discussed above, there are numerous methods by which a label of a signal producing system can produce a signal detectable by external means. Activation of a signal producing system depends on the nature of the signal producing system members.

Temperatures during measurements generally range from about 10° to about 70° C., or from about 20° to about 45° C., or about 20° to about 25° C., for example. In one approach standard curves are formed using known concentrations of the analyte. Calibrators and other controls may also be used.

Luminescence or light produced from any label can be measured visually, photographically, actinometrically, spectrophotometrically or by any other convenient means to determine the amount thereof, which is related to the amount of analyte in the medium. The examination for one or both of the presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, or chemiluminometer, for example.

Kits Comprising Reagents for Conducting Assays

Embodiments of the present compositions and other reagents for conducting a particular assay for an analyte may be present in a kit useful for conveniently performing an assay for the determination of an analyte. In some embodiments a kit comprises in packaged combination a composition in accordance with the principles described herein. In some embodiments, depending on the nature of an assay, the kit also includes an acridinium-labeled antibody for the analyte or an acridinium-labeled analyte analog. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, sps members and ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay utilizing embodiments of the present compositions. The kit can further include a written description of a method as described above.

Definitions

The following definitions are provided for terms and phrases not otherwise specifically defined above.

The phrase "at least" as used herein means that the number of specified items may be equal to or greater than the number recited.

The phrase "about" as used herein means that the number recited may differ by plus or minus 10%; for example, "about 5" means a range of 4.5 to 5.5.

The designations "first," "second" and "third" are used solely for the purpose of differentiating between two or more items such as, for example, "first sps member" and "second sps member," or "first polymerized monomer," "second polymerized monomer" and "third copolymerized monomer and are not meant to imply any sequence or order or importance to one item over another or any order of addition, for example.

The following examples further describe specific embodiments of the invention by way of illustration and not limitation and are intended to describe and not to limit the scope of the invention. Parts and percentages disclosed herein are by volume unless otherwise indicated.

EXAMPLES

Materials:

Unless indicated otherwise, reagents were purchased from Sigma-Aldrich (Milwaukee, Wis.) and used as received unless indicated otherwise.

Abbreviations:
BSA bovine serum albumin
BgG bovine gamma globulin
TG monomeric bovine thyroglobulin
T4 thyroxine
DMSO dimethylsulfoxide
AIBN azobis(isobutyronitrile)
PEG poly(ethylene glycol)
MPEG monomethoxy-poly(ethylene glycol)
NaCNBH$_3$ sodium cyanoborohydride
MAMDMA methacrylamidoacetaldehyde dimethyl acetal
HEMA 2-hydroxyethylmethacrylate
THF tetrahydrofuran
HCl hydrochloric acid
OH hydroxyl group
NaOH sodium hydroxide
Acetate buffer 0.1 M sodium acetate acetic acid buffer pH 5.0
DMF dimethyl formamide
DMAP 4-N,N-dimethylamino-pyridine
MA.Actl methacrylamidoacetaldehyde
DSC disuccinimidyl carbonate
BCA bicinchoninic acid
ANS anilinonaphthalene sulfonic acid
UPA Ultra Particle Analyzer
hr(s) hour(s)
min minutes
DI deionized
w/w weight to weight
rpm rotations per minute
mL milliliters
mg milligrams
g grams
mM millimolar
RT room temperature
Da daltons
kDa kilodaltons
nd not determined
Preparation of Reagents Example 1: Synthesis of MAMDMA (FIG. 1)

Methacrylic acid (9.0 g, 0.1 mole) and N-hydroxysucinimide (11.5 g, 0.1 mole) were placed in a round bottom flask and dissolved in 300 mL of THF. The solution was cooled in an ice bath. Dicyclohexyl carbodiimide (21.0 g, 0.1 mole) dissolved in 50 mL THF was added. The reaction mixture was stirred for 2 hrs in an ice bath. Aminoacetaldehyde dimethyl acetal (15.0 g, 0.1 mole) and triethylamine (15.0 g, 0.15 mole) were added. The reaction mixture solidified to a cake and became difficult to stir due to this addition. An additional 300 mL THF was added. The reaction mixture was warmed up to room temperature and stirred for 3 days. Reaction mixture was filtered to remove precipitated solids. The clear solution was concentrated under reduced pressure. MAMDMA was obtained as a viscous liquid. Yield: 20.0 g, 90%. $^1$H NMR (CDCl$_3$): 5.4 δ 1H, 5.6 δ 1H (double bond protons), 3.5 δ 6H (acetal protons) 3.1 δ 1H (—C$\underline{H}$—(OCH$_3$)$_2$), 2.5 δ 2H (—C$\underline{H_2}$—CH—), 2.3 δ 1H (—N$\underline{H}$—), 1.8 δ 3H (=C—C$\underline{H_3}$).

Figure 2:
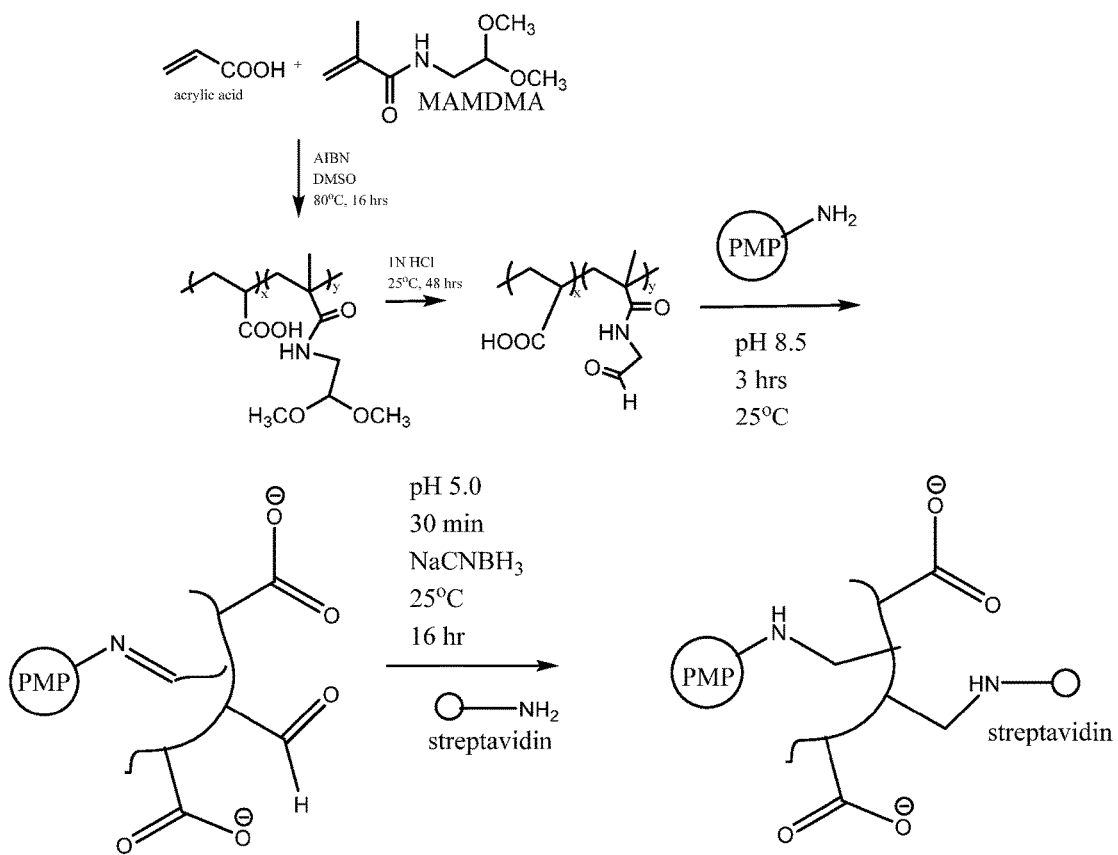
FIG. 2 is a schematic diagram of a synthesis of paramagnetic particles (PMP) coated with poly (acrylic acid-co-MA-Actl)-streptavidin.

Example 2: Synthesis of poly(acrylic acid-co-methacrylamidoacetaldehyde) (poly(acrylic acid-co-MA-Actl)) (FIG. 2)

Preparation of poly(acrylic acid-co-MAMDMA).
In a round bottom flask equipped with an argon gas inlet and outlet, 2.5 g MAMDMA prepared as described above, 1.1 g acrylic acid (AA), 0.07 g AIBN (MAMDMA:AA:AIBN 1:1:0.03) were dissolved in 60 mL DMSO. Argon gas was purged through DMSO solution at room temperature for 30 min. The flask containing monomer solution was immersed in an oil bath pre-heated to 80° C. Polymerization was conducted at 80° C. for 16 hrs under Argon purging. Polymer solution was poured into 700 mL diethyl ether to precipitate the polymer. The polymer was dissolved in 300 mL water and concentrated to 32.5 mL using CENTRICON® Plus-70 filter cups having a molecular weight cut off of 3,000 Da at 4° C. at 4000 rpm for 3 times at 45 min each. Total polymer yield after purification=1.61 g.

Hydrolysis of the Acetal Groups of the poly(acrylic acid-co-MAMDMA) to Form poly(acrylic acid-co-MA-Actl).

A solution of 1.61 g poly(acrylic acid-co-MAMDMA) from above in 32.5 ml water was added to 40 ml water 1N HCl. The solution was stirred at room temperature for 36 hrs. Then, the pH of the solution was adjusted to 5.0 using 10N NaOH, HCl, and acetic acid. The polymer solution of pH 5.0 (280 ml) was concentrated to 70 ml by centrifugation in a CENTRICON® Plus-70 filtration cups of 3,000 molecular weight cutoff at 4° C. at 4000 rpm for 2 times 45 min. Final 37.5 ml solution obtained as retentate was stored at 4° C. Solids content of the hydrolyzed polymer solution was determined. Total polymer yield after purification=2.08 g (some salt remained in solution after diafiltration). Polymer solution was stored at 4° C.

Preparation of Paramagnetic Particle (PMP) Coated with Poly (acrylic acid-co-MA-Actl)-Streptavidin (FIG. 2):

Alkylamine paramagnetic particles (PMP) solution was rocked at room temperature for 1 hr. The alkylamine PMP were paramagnetic particles having an Fe(II) oxide and Fe(III) oxide core and a coating of polysiloxane containing amine groups on the surface. PMP were prepared by first co-precipitating Fe(II) and Fe(III) salts in presence of a base and completing oxidation by heating the precipitated particles followed by contacting the oxide particles with a polysiloxane containing amine. Aliquots (50 mg) of PMP (51.3 mg/mL) were taken for each lot, totaling six lots. The PMP were washed 3 times (35 mL per wash) with 0.02M Na$_3$PO$_4$ pH 7.75. Poly(AA-co-MA-Actl) (282 mg) prepared as described above was combined with each of the washed 50 mg aliquots of PMP. Then, the pH of each lot was adjusted from about 5.5 to 8.6+/−0.1 using 0.1M Na$_2$CO$_3$, pH 9.5. PMP plus polymer suspension was incubated at 25° C. for 3 hrs. Polymer coated PMP were separated magnetically, and supernatant solution was removed. In this manner, polymer coated PMP were washed 3 times (35 mL per wash) with 0.02M Na$_3$PO$_4$ pH 7.75. Washing was conducted by rocking at 25° C. for 3 hrs. After decantation in the final wash, each lot/aliquot of PMP received a unique amount of streptavidin (45, 90, 135, 200, 300, and 500 mg, respectively). The streptavidin solutions were each dissolved in 3 mL of 0.1M Acetate Buffer pH 5.0. Then the PMP-copolymer-streptavidin (SAV-copolymer-PMP) solutions were rocked at room temperature for 30 min. Next, 30 mg of NaCNBH$_3$ was added to each, followed by rocking overnight at 25° C. The supernatant was decanted and PMP were washed 3 times using 1M NaCl, pH 7.0. Next, the SAV-copolymer-PMP were washed 2 times with a buffer (50 mM NaPO$_4$, 150 mM NaCl, 15 mM NaN$_3$ pH 7.4). Then, the SAV-copolymer-PMP were resuspended with ~3 mL of the same buffer. Finally, solids content was determined, BCA Assay was performed on the initial and after-reaction supernatants obtained to determine the protein concentration on the beads, and particle size was measured (MICROTRAC® UPA) at 0.2 mg/ml. Streptavidin loading on the SAV-copolymer-PMP increased from 0.25-1.5 mg/mg as challenged protein amount increased from 45-500 mg. Particle size of the SAV-copolymer-PMP was ~2 microns.

Figure 3:
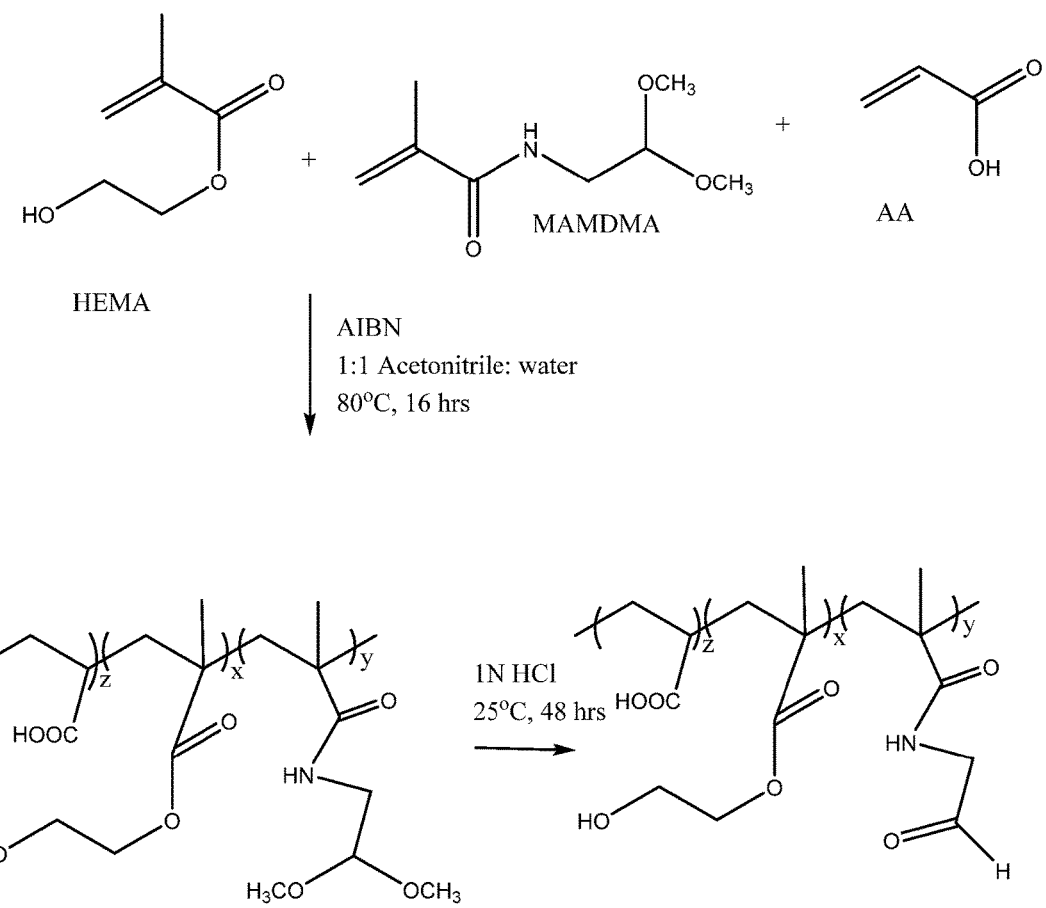
FIG. 3 is a schematic diagram of a synthesis of a copolymer with three monomers copolymerized.

Example 3: Preparation of a Copolymer with Three Monomers Copolymerized (poly(HEMA-co-AA-co-MA-Actl) (FIG. 3)

In a round bottom flask equipped with an argon gas inlet and outlet, 3.4 g MAMDMA, 2.6 g HEMA, 1.4 g acrylic acid, 0.1 g AIBN were dissolved in 100 mL acetonitrile and 100 mL water. Argon gas was purged through the solution at room temperature for 30 min. The flask containing monomer solution was immersed in an oil bath pre-heated to 80° C. Polymerization was conducted at 80° C. for 16 hrs under argon purging using a reflux condenser to prevent solvent evaporation. Then, the polymer solution was concentrated in vacuo to remove acetonitrile. Aqueous polymer solution was diluted to 500 ml and 50 mL 5N HCl was added. The reaction mixture was stirred at room temperature for 2 days. There was significant polymer precipitation as evidenced by a precipitated white mass. Solids were separated by centrifugation at 300 rpm for 20 min at 4° C. Then, the reaction mixture was cooled to 4° C. for 1 hr and the pH was adjusted to 5.2 using 10 N NaOH and glacial acetic acid. The solution was centrifuged at 3500 rpm for 20 min at 4° C. Clear solution was decanted and concentrated from 500 mL to 20 mL using CENTRICON® diafiltration cups of having a molecular weight cutoff of 3000. Solids content in concentrated/diafiltered polymer solution was determined. The yield of polymer recovered was 1.584 g.

Figure 4:
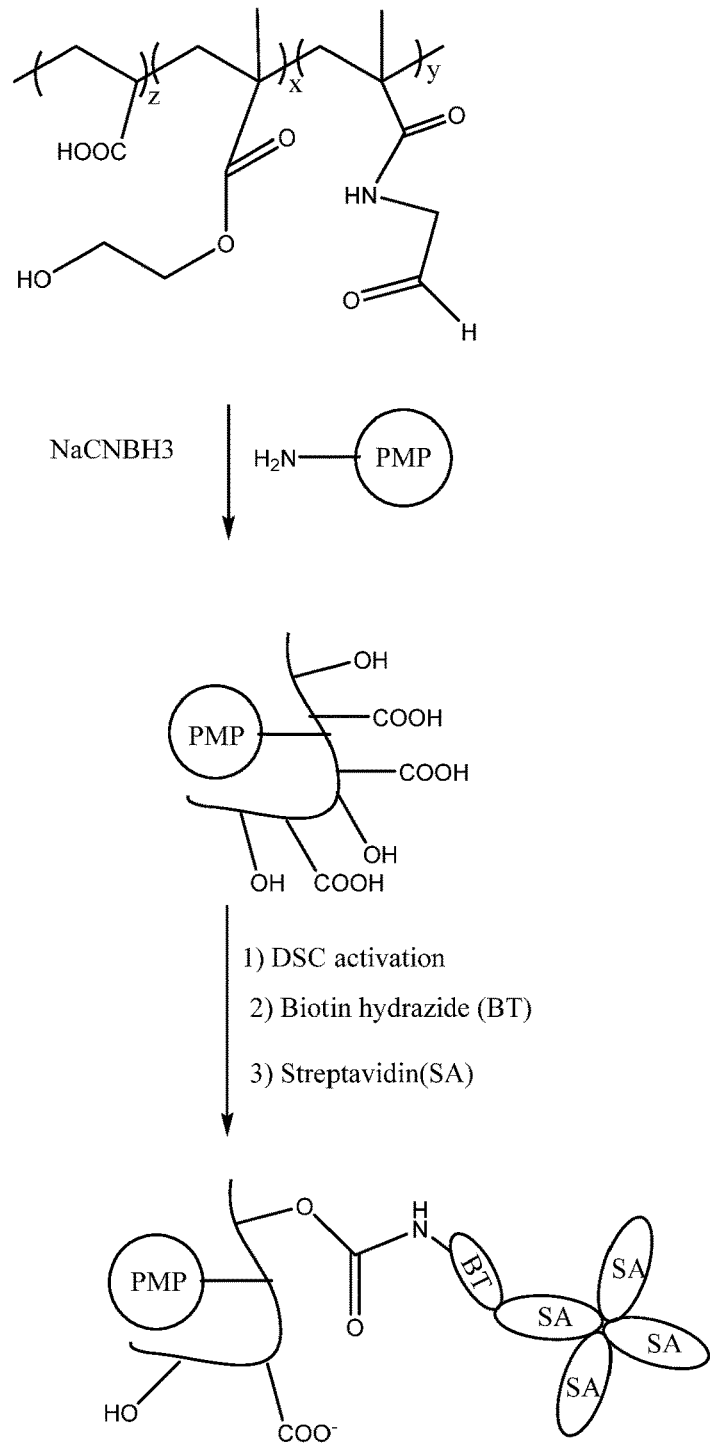
FIG. 4 is a schematic diagram of a synthesis of PMP coated with poly(HEMA-co-AA-co-MA-Actl)-streptavidin (SA).

Example 4: Preparation of PMP Coated with Poly(HEMA-co-AA-co-MA-Actl), Conjugated to Biotin Through Hydroxyls on Copolymer, and Streptavidin Captured Thereon (FIG. 4)

PMP Coating with poly(HEMA-co-AA-co-MA-Actl) and OH Activation by DSC (DSC-Activated PMP):

100 mg PMP (prepared as described above) and 400 mg poly(HEMA-co-AA-co-MA-Actl) (prepared as described above) in 5 mL solution of 0.1M acetate buffer, pH 5.0, were mixed together. The pH was adjusted to 8.0-8.5 using sodium carbonate and HCl. The suspension was rocked gently at room temperature for 30 min. Then, 90 mg of NaCNBH$_3$ was added and the solution was allowed to rock at 25° C. overnight. Then, the PMP were washed three times with 40 mL 0.02M sodium phosphate buffer, pH 7.2, twice with 50 mL DI water, and then three times with 40 mL DMF. Then, 40 mL DMF were added and the PMP were transferred to a 25 mL round bottom flask. To this were added 500 mg DSC and 50 mg DMAP and the reaction mixture was stirred at RT for approximately 48 hrs. PMP were magnetically separated and DMF removed.

Conjugation of Biotin-Hydrazide to DSC-Activated PMP (Biotinylated DSC-Activated PMP):

To the PMP from above was added 50 mg biotin-hydrazide in 30 mL 0.02M sodium phosphate buffer, pH 7.7, and the mixture was stirred overnight at RT overnight. The following day, PMPs were magnetically separated and washed three times with 40 mL 50 mM pH 7.0 sodium phosphate buffer.

Streptavidin Capturing on Biotinylated PMP:

The biotinylated DSC-activated PMP from above were suspended in 15 mL pH 7.0 phosphate buffer (50 mM) containing 15 mg streptavidin. The suspension was kept at 25° C. on a rocker for overnight. Supernatant was collected and streptavidin-PMP were washed three times with 40 mL pH 7.0 phosphate buffer and were then suspended in 10 mL phosphate buffer. Negligible protein was found in supernatant indicating all 15 mg of streptavidin became bound to DSC-activated PMP.

Figure 5:
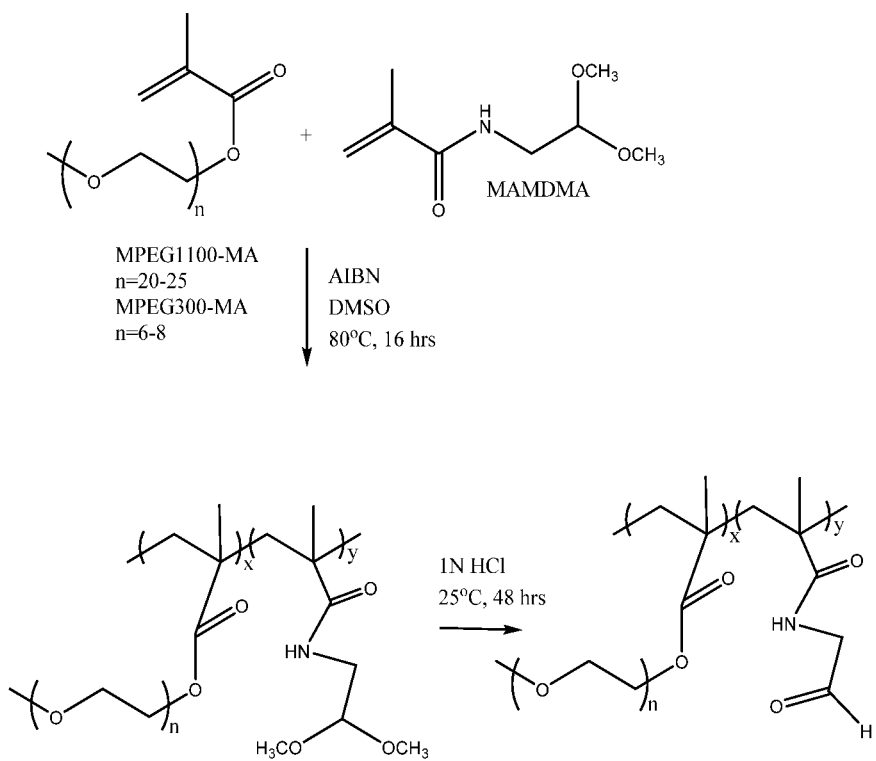
FIG. 5 is a schematic diagram of a synthesis of poly (MPEG1100-MA-co-MA-Actl) and poly(MPEG300-MA-co-MA-Actl).
Figure 6:
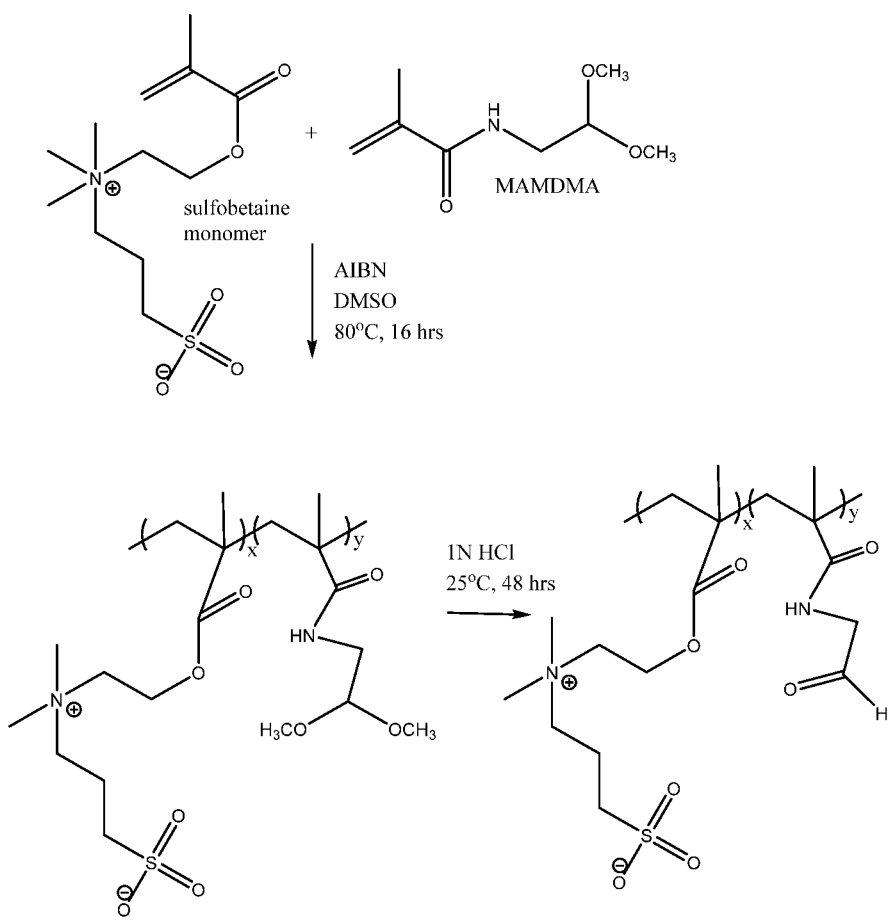
FIG. 6 is a schematic diagram of a synthesis of poly (sulfobetaine-MA-co-MA-Actl).
Figure 7:
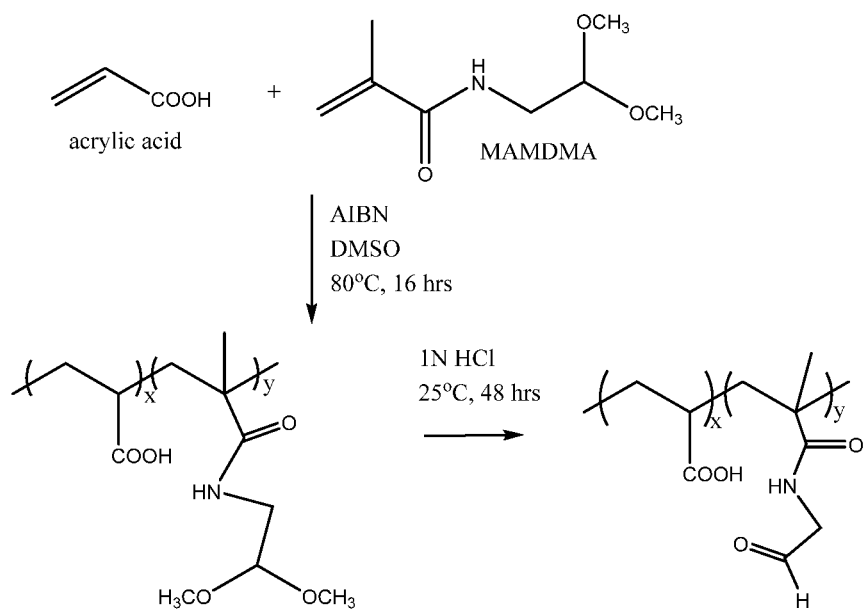
FIG. 7 is a schematic diagram of a synthesis of poly(AA-co-MA-Actl).

Example 5: Preparation of poly(MPEG1100-MA-co-MA-Actl) and poly(MPEG300-MA-co-MA-Actl) (FIG. 5), poly(sulfobetaine-MA-co-MA-Actl) (FIG. 6) and poly(AA-co-MA-Actl) (FIG. 7)

Procedure for Polymerization of MAMDMA with Different Monomers:

In a round bottom flask equipped with Argon gas inlet and outlet, MAMDMA (0.01M), hydrophilic monomer (0.01 mole) and AIBN (0.0001 mole, [Monomer]/[AIBN]=200) were dissolved in 30 mL DMSO. Argon gas was purged through the DMSO solution at room temperature for 30 min. The flask containing monomer solution was immersed in oil bath pre-heated to 80° C. Polymerization was conducted at 80° C. for 16 hrs under Argon purging. DMSO solution was poured into 700 mL diethyl ether to precipitate the polymer. The polymer was dissolved in 100 mL water and concentrated to 10-15 mL using an ultrafiltration membrane of molecular weight cut off 5,000 Da.

Procedure for Hydrolysis of Acetal Groups to Obtain Aldehyde Containing Synthetic Copolymers:

An aqueous solution (100 mL) containing 2-3 g copolymer synthesized as above was taken in an Erlenmeyer flask. To this, 100 mL 1N HCl was added. The acidic solution was stirred for 2 days at room temperature; pH of the solution was adjusted to 5.0 with the addition of concentrated NaOH and acetic acid. Presence of aldehyde groups in the copolymer was qualitatively confirmed by purpald assay (Dickinson, R. G.; Jacobsen, N. W., Chemical Communications, p. 1719 (1970). The copolymer solution was concentrated to 10 mL using an ultrafiltration membrane of molecular weight cut off 5,000 daltons. Aqueous polymer solutions (100-150 mg solids/mL) were stored at 4° C. The different copolymers prepared are set forth in Table 1.

TABLE 1

Molecular weight characterization of aldehyde-containing copolymers

| Polymer | MW (Da) | Polydispersity index |
| --- | --- | --- |
| Poly(sulfobetaine-co-MA-Actl) (1:1) | 155,800 | 1.57 |
| Poly(MPEG$_{1100}$-MA-co-MA-Actl) (1:1) | 65,990 | 4.5 |
| Poly(AA-co-MA-Actl) (1:1) | 22,490 | 1.34 |
| Poly(MPEG$_{300}$-MA-co-MA-Actl) (1:1) | nd | nd |

Figure 8:
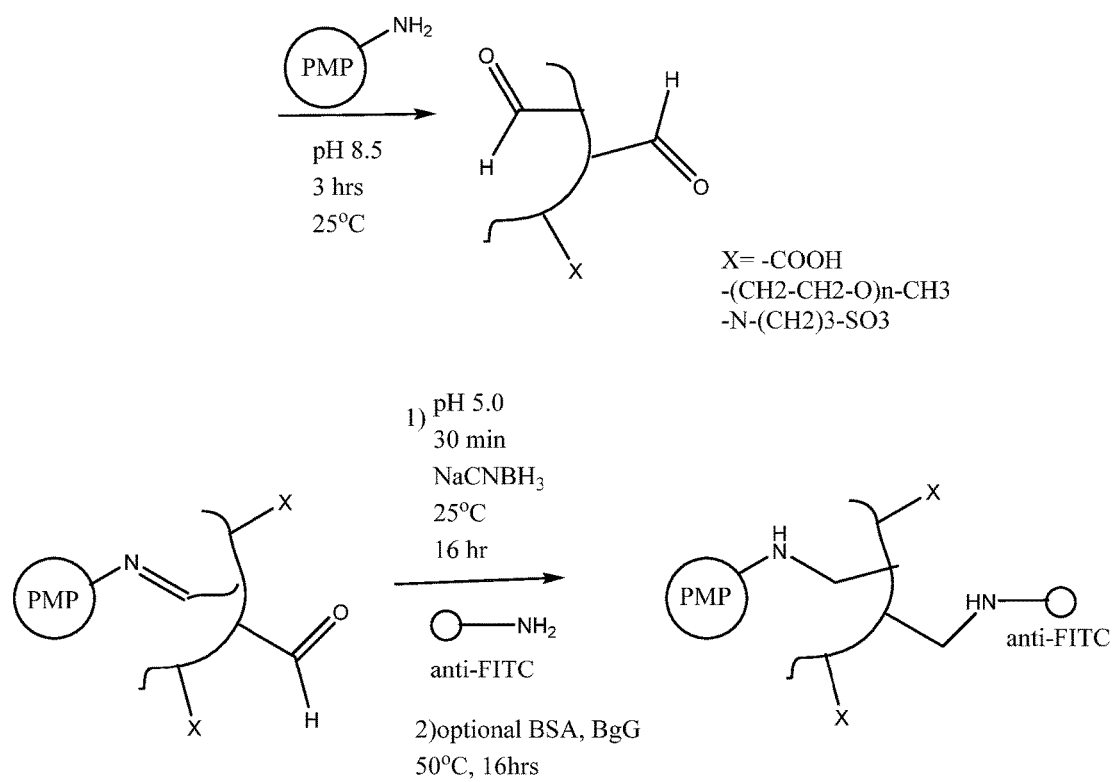
FIG. 8 is a schematic diagram of a synthesis of copolymer-coated PMP-anti-FITC conjugates.

Example 6: Preparation of PMP Coated with Copolymers and Anti-FITC Conjugated to Copolymers (Copolymer-Coated PMP-Anti-FITC Conjugates) (FIG. 8)

Synthesis of Heat Stressed PMP Coated with Synthetic Copolymers and Anti-FITC:

The term "heat stressed PMP" refers to PMP (which have a coating of copolymer and sbp member) that have been contacted with a buffer (such as, for example, a phosphate buffer containing BSA and BgG) (heat stressing buffer) at a temperature that is higher than ambient temperature (such as, for example, a temperature greater than 40° C., or greater than 50° C., or greater than 60° C.) for a period of time (such as, for example, about 16 to about 48 hrs, or about 16 to about 24 hrs, or about 24 to about 48 hrs). PMP (100 mg in 2 mL) were taken in each of three falcon tubes. To each tube, 10 ml each 0.02 M phosphate buffer pH 7.4 was added and mixed well for 30 min on a rotating table. Then, the particles were separated magnetically and phosphate buffer was decanted. Fresh phosphate buffer was added and the PMP were rewashed as above and magnetically separated.

To each PMP preparation above was added 6 ml copolymer solution (100-150 mg/ml) and the pH was adjusted to 8.5 using 0.1 M Na$_2$CO$_3$. The tubes were kept on a rocker at 25° C. for 3 hrs. The copolymers used were: poly (MPEG300-MA-co-MA-Actl), poly(MPEG1100-MA-co-MA-Actl), and poly(sulfobetaine-MA-co-MA-Actl). Copolymer-coated PMP were washed twice using 12 ml 0.02 M phosphate buffer pH 7.4 as described above.

To each copolymer-coated PMP preparation was added 6 ml anti-FITC (5 mg/ml, 30 mg total) in 0.02 M phosphate buffer pH 7.7. Particles were mixed gently for 30 min and 30 mg NaCNBH$_3$ was added and the mixture was kept on a rocker at 25° C. for 16 hrs.

Then, copolymer-coated PMP-anti-FITC conjugates were separated magnetically and the supernatant was preserved for remaining protein content determination. PMP were washed twice with 12 ml phosphate buffer as described above. Then, the PMP were washed twice with 12 ml protein wash buffer (50 mM phosphate buffer containing 150 mM NaCl and BSA and BgG, pH 7.4). Finally, PMP were incubated with 12 ml each protein wash buffer at 50° C. for 16 hrs while mixing gently on a rocker.

Heat stressed PMP were allowed to cool to 25° C. and separated magnetically. Heat stressed PMP were washed twice with 12 ml protein wash buffer and once with 12 ml protein storage buffer (protein wash buffer containing sodium azide) as described above. Finally, the heat stressed PMP were suspended in 10 ml protein storage buffer and kept at 4° C. until further use. Anti-FITC loading on PMP was determined from the difference in protein concentration measured before and after PMP conjugation. Anti-FITC loading data obtained from BCA assay and BSA standard plot is summarized in Table 2.

TABLE 2

| Description | Anti-FITC added (mg) | Anti-FITC recovered (mg) | Anti-FITC bound (mg/mg) | Conjugation efficiency (%) |
|---|---|---|---|---|
| PMP coated with poly(MPEG300-MA-co-MA-Actl) and Anti-FITC | 30 | 21 | 0.09 | 30 |
| PMP coated with poly(MPEG1100-MA-co-MA-Actl) and Anti-FITC | 30 | 16.6 | 0.134 | 44 |
| PMP coated with poly(sulfobetaine-MA-co-MA-Actl) and Anti-FITC | 30 | 15.5 | 0.145 | 48 |

Synthesis of Non-Heat Stressed PMP Coated with Synthetic Copolymers and Anti-FITC:

PMP were coated with copolymers and anti-FITC as described above in Example 6 except that no heat stressing of PMP was done.

Figure 9:
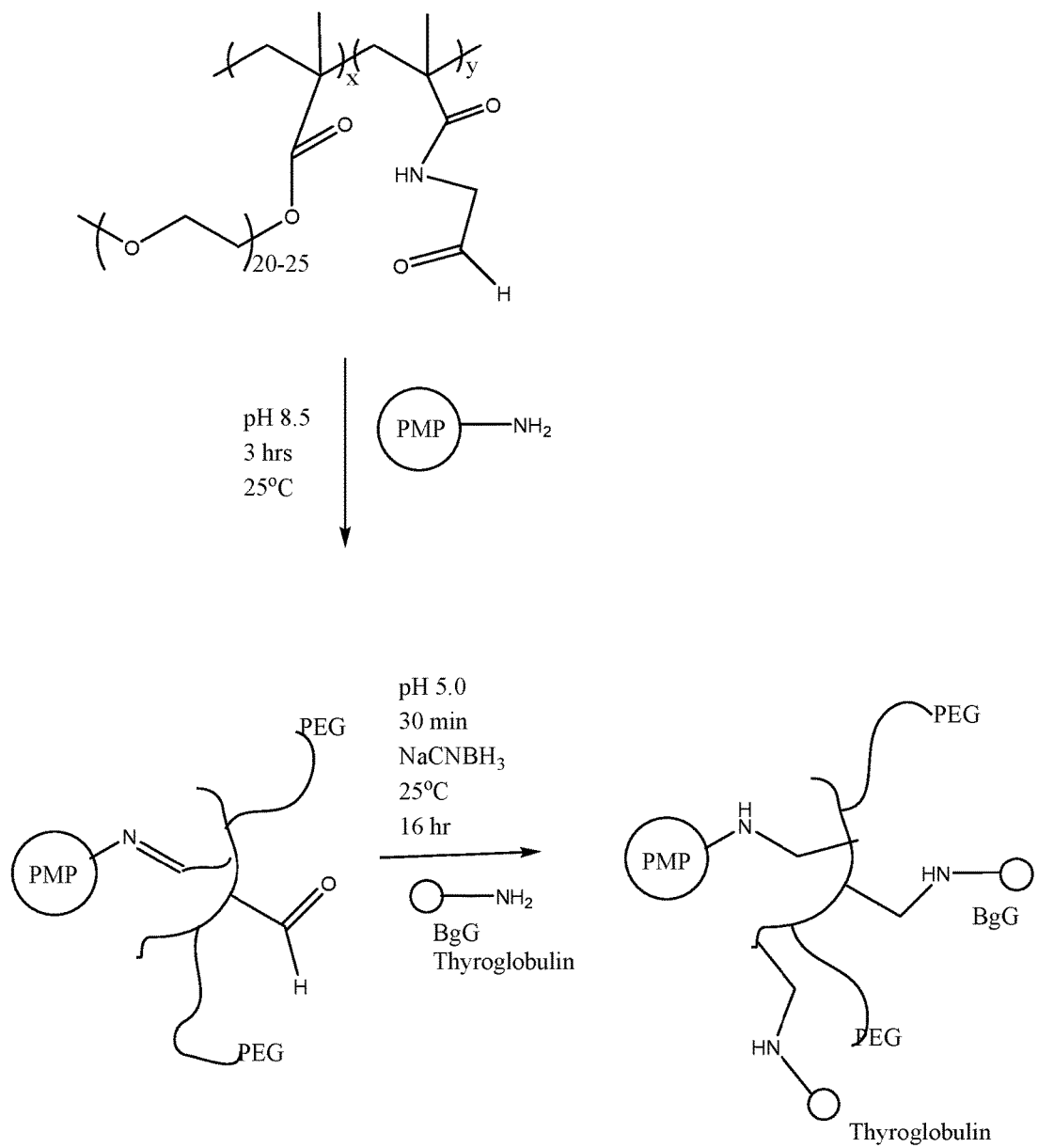
FIG. 9 is a schematic diagram of a synthesis of copolymer-coated PMP with BgG and TG bound thereto.

Example 7: Preparation of PMP Coated with Copolymer and BgG and TG (FIG. 9

Preparation of poly (MPEG1100-MA-co-MA-Actl):
MAMDMA (2.5 g, 0.014M), MPEG1100-MA (6.25 g, 0.005 M), AIBN (62.6 mg, 0.00037 M), and DMSO (31.3 mL) were placed in a 250 mL round bottom flask equipped with Argon gas inlet and outlet. The mixture was purged with argon for 30 min at RT while stirring. The flask was placed in an oil bath preheated to 80° C. while stirring. Polymerization was conducted at 80° C. for 16 hrs under continuous argon purging. The above DMSO medium was poured into 700 mL diethyl ether and stirred for 1 hr at room temperature to precipitate polymer, which was poly (MPEG1100-MA-co-MAMDMA). The supernatant, which contained diethyl ether, was decanted. The polymer was dissolved in 200 mL deionized (DI) water and purified by ultrafiltration (AMICON® CENTRICON®, Millipore Corporation, Billerica, Mass.) two times using a membrane of molecular weight cut off 30 kDa. The polymer was diluted to a solid content of 45 mg/mL in DI water, amounting to 5.4 g in 120 mL. This polymer solution (2.7 g) was mixed with 200 mL of DI water and 20 mL of 5 N HCl, and the mixture was stirred at RT for 48 hrs. The pH was adjusted to 5.0 using NaOH and acetic acid. The final polymer had a solid content of 77 mg/mL in DI water, amounting to about 3 g. Some of this solids content consisted of NaCl and sodium acetate. The polymer was stored at 2-8° C.

Preparation of PMP-poly (MPEG1100-co-MA-Actl)-BgG/TG:
PMP solution (PMP in DI water) was rocked at room temperature for 1 hr. Aliquots of 600 mg of PMP were taken. PMP were washed 3 times (40 ml per wash) with 0.02M NaPO4 pH 7.75. A PMP-polymer solution was formed by combining 81 ml (6.48 g) of poly (MPEG1100-co-MA-Actl) with a washed 600 mg aliquot of PMP. Then, the pH of the PMP-polymer solution was adjusted from ~5.5 to 8.5+/−0.1 using 0.1M NaCO3, pH 9.5. The solution was rocked at 25° C. for 3 hrs. PMP were then washed 3 times (40 ml per wash) with 0.02M NaPO4 pH 7.75. After the final wash was decanted, 600 mg of TG and 1200 mg of BgG were combined in 30 ml of 0.1M acetate buffer pH 5.0 (60 mg/ml protein solution) and added to the PMP-polymer solution. Then, the PMP-polymer-TG/BgG solution was rocked at RT for 30 min. Next, 360 mg of NaCNBH$_3$ was added and the solution was rocked overnight at 25° C. The initial supernatant was decanted and PMP were washed 3 times using 1M NaCl. BCA Assay was performed to determine the protein concentration in the supernatants prior and during NaCl washes. Next, the beads were washed 2 times with 50 mM NaPO$_4$, 150 mM NaCl, 15 mM NaN$_3$ pH 7.4 buffer. PMP were then resuspended with about 45 ml of the same buffer and filtered through a 41 um mesh. Finally, solids content was determined along with particle size (MICROTRAC® UPA at 0.2 mg/ml). The results were as follows: 13.4 mg/ml, final concentration x 43 ml=576 mg final yield; 0.69 mg of protein (BgG/TG) bound per mg of PMP; 0.51 (45%) and 2.38 (55%) micron particle size.

Assays

Example 8: T4 Assay Using poly(MPEG1100-MA-co-MA-Actl)-coated PMP

All T4 assays were performed on a CENTAUR® apparatus (Siemens Healthcare Diagnostics Inc., Newark Del.) (Siemens). The details of the assay were as follows: PMP-poly(HEMA-co-AA-co-MA-Actl)-Biotin-Streptavidin PMP were diluted to 132 µg/mL by adding 16.5 mL of particles to 483.5 mL of T4 solid phase buffer (50 mM sodium barbital, 150 mg/L ANS ammonium, 0.25% PROBUMIN®, 0.002% BgG, 50 mM sodium phosphate monobasic monohydrate, 0.44 g/L tetrasodium EDTA, 0.5 mL/L mouse serum, 0.1% sodium azide, final pH 6.00). Reagent packs were made by adding 25 ml of prepared solid phase reagent to the S-Channel of the CENTAUR® Readypack (a container storing different assay reagents used in assay), while commercial Lite reagent (anti T4-2',6'-dimethylcarbonylphenyl-10-sulfopropylacridinium-9-carboxylate 4'-NHS ester conjugate (Anti-T4-NSP-DMAE-NHS) and ancillary well reagent were used in their respective wells in the Readypack.

Calibration curves were established by running T4 standards on a CENTAUR® instrument for each experimental reagent condition used for on-board stability. The onboard stability experiment was conducted for 28 days. Test point runs were done on days 0, 4, 8, 12, 17, 20, 24 and 28. PMP, samples (containing T4, details below) and anti-T4-NSP-DMAE-NHS conjugate were incubated for a method specific amount of time, separated magnetically, and acridinium ester in separated complex was activated by an activator and light emitted was recorded by the instrument. Results obtained were converted into % recovery of original signal before the start of the on-board stability experiment. The results obtained are summarized in Table 3. Percent (%) recovery of 100+/−10% was considered as indicative of copolymer coated PMP onboard stability. Samples tested were as follows:
CA76HB=21.6 µg/dL T4
CA76LB=3.71 µg/dL T4
K40781=9.11 µg/dL T4
K40782=11.3 µg/dL T4
K40783=15.6 µg/dL T4
The results are summarized in Table 3.

phosphate, 140 mM NaCl, 0.1% BSA, 0.1% Triton® X-100, pH 7.2 buffer after stress testing, while the other was not. The tubes were incubated at 4° C. (control condition) or 45° C. (test condition) for varying amounts of time. On day 21, one tube from each pair was buffered-exchanged with 50 mM sodium phosphate, 140 mM NaCl, 0.1% BSA, 0.1% Triton® X-100, pH 7.2 buffer by magnetic separation followed by vacuum aspiration of the liquid medium. 4.5 mL of buffer from 4° C. storage was then added to the buffer-exchanged tubes. The eight samples were then tested on a Siemens Centaur® XP immunochemistry analyzer.

Figure 10:
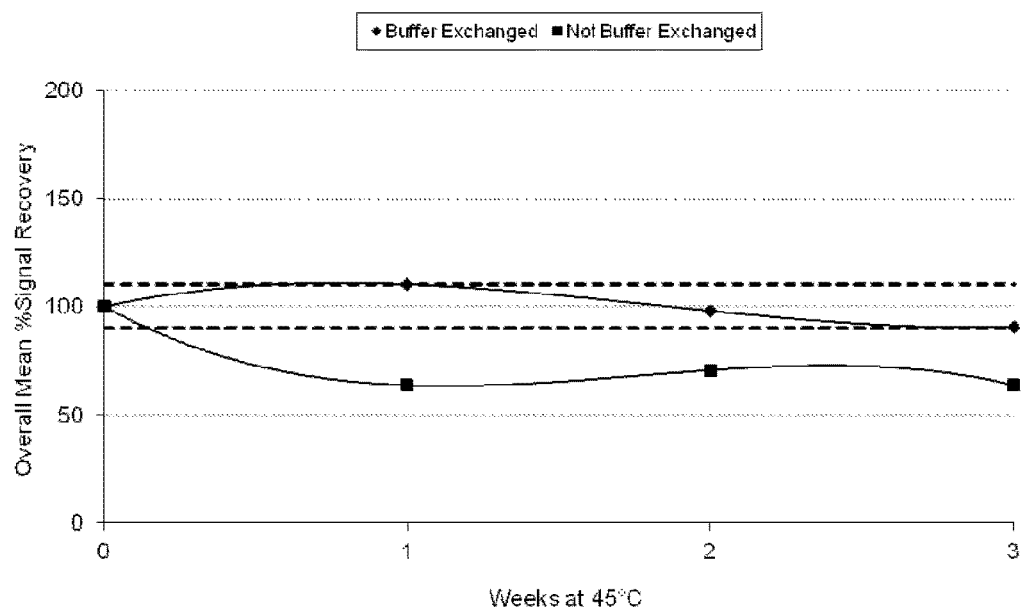
FIG. 10 is a graphic depiction of results obtained in Folate assay using poly(HEMA-co-AA-co-MA-Actl)-Biotin-Streptavidin-coated PMP and performed on a CENTAUR® apparatus (Siemens Healthcare Diagnostics Inc., Newark Del.) Results obtained were interpreted graphically as percent (%) recovery versus time.

For the testing, PMP-poly(HEMA-co-AA-co-MA-Actl)-Biotin-Streptavidin samples were placed into the solid-phase well of a Centaur® ReadyPack (a container storing different assay reagents used in assay), while commercial Lite reagent (Folate-succinimidyl-diaminoethyl-DMAE ester) and ancillary well reagent were used in their respective wells. Each of the eight packs were then used to test six serum samples (in triplicate) with known folate values of 2.24, 3.69, 7.65, 11.81, 19.45 & 31.19 ng/mL, in order to generate mean signal values in Relative Light Units (RLU) for each sample at each condition. Sample, Lite reagent, and PMP were incubated for 7 minutes, and PMP were separated magnetically and treated with an activating reagent to activate acridinium ester to emit light. Emitted light was measured by the Centaur® instrument and results were provided by the instrument's computing system. Results obtained were interpreted graphically as % recovery vs. time and are depicted in FIG. 10.

All publications and patent applications cited in this specification are herein incorporated by reference as if each individual publication or patent application were specifically and individually indicated to be incorporated by reference.

Although the foregoing invention has been described in some detail by way of illustration and example for purposes

TABLE 3

| Sample ID (conc. Units) | % Recovery | | | | | | |
|---|---|---|---|---|---|---|---|
| | Day 4 | Day 8 | Day 12 | Day 17 | Day 20 | Day 24 | Day 28 |
| CA76HB (21.6 µg/dL) | 104.5% | 99.7% | 102.9% | 107.9% | 104.0% | 102.9% | 108.3% |
| CA76LB (3.71 µg/dL) | 90.0% | 113.3% | 106.3% | 105.8% | 104.2% | 107.0% | 106.9% |
| K40781 (9.11 µg/dL) | 102.9% | 105.8% | 101.6% | 105.3% | 102.6% | 102.5% | 105.7% |
| K40782 (11.3 µg/dL) | 101.1% | 103.4% | 103.2% | 107.6% | 101.0% | 101.0% | 104.9% |
| K40783 (15.6 µg/dL) | 99.3% | 104.2% | 101.2% | 106.0% | 99.9% | 103.9% | 102.0% |

Example 9: Folate Assay Using poly(HEMA-co-AA-co-MA-Actl)-Biotin-Streptavidin-Coated PMP All folate assays were performed on a CENTAUR® apparatus (Siemens). The details of the assay were as follows: PMP-poly(HEMA-co-AA-co-MA-Actl)-Biotin-Streptavidin were diluted to 200 µg/mL by adding 899 µL of beads to 39.101 mL of buffer (50 mM sodium phosphate, 250 mM NaCl, 0.1% sulfhydryl-modified BSA, 0.1% Triton®-X-100, 0.05% Proclin-300, pH 7). Eight 4.5 mL aliquots of 200 µg/mL PMP-poly(HEMA-co-AA-co-MA-Actl)-Biotin-Streptavidin were then prepared in 5 mL polypropylene tubes (with gaskets and internal threads), which were then subjected to parafilming. The tubes were then divided into 4 pairs, representing 4 test conditions. One tube from each pair was buffer exchanged with 50 mM sodium of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of determining in a sample the presence and/or amount of an analyte, the method comprising:
   (a) providing in combination in a medium:
      (i) the sample,
      (ii) a member of a signal producing system (A) bound to a member of a specific binding pair that specifically binds to the analyte or (B) bound to an analyte analog, and
      (iii) a paramagnetic metal oxide solid support associated with a member of a specific binding pair that specifically binds to the analyte or associated with a member of a specific binding pair that is bound to a member of a specific binding pair member that specifically binds to the analyte;
      wherein the paramagnetic metal oxide solid support comprising a coating of a synthetic copolymer wherein the synthetic copolymer comprises three of a first copolymerized monomer, a second copolymerized monomer and a third copolymerized monomer and wherein the synthetic copolymer comprises a polyethylenic backbone and wherein:
         (i) the first copolymerized monomer comprises a pendant moiety of the formula: —C(O)—O—(CH$_2$CH$_2$O)$_m$—Z, wherein:
         Z is H or alkyl of from 1 to 6 carbon atoms,
         m is 1 to 100;
         (ii) the second copolymerized monomer comprises a pendant moiety of the formula:
         -OC(O)NR-J wherein R is H or alkyl of from 1 to 6 carbon atoms and J is the member of a specific binding pair; and
         (iii) the third copolymerized monomer comprises a pendant moiety of the formula: —COOH or a derivative thereof,
   (b) subjecting the combination to conditions for forming a complex,
   (c) separating the solid support from the medium, and
   (d) activating the member of the signal producing system bound to the separated solid support and detecting the amount of the complex, the amount of the complex being related to the presence and/or amount of analyte in the sample.

2. A method of determining in a sample the presence and/or amount of an analyte, the method comprising:
   (a) providing in combination in a medium:
      (i) the sample,
      (ii) a member of a signal producing system bound to a member of a specific binding pair that specifically binds to the analyte or bound to an analyte analog, and
      (iii) a composition comprising:
      a paramagnetic particle comprising:
         (A) a member of a specific binding pair that specifically binds to the analyte or a member of a specific binding pair that is bound to a member of a specific binding pair member that specifically binds to the analyte, and
         (B) a coating of a synthetic copolymer wherein the synthetic copolymer comprises three of a first copolymerized monomer, a second copolymerized monomer and a third copolymerized monomer and wherein the synthetic copolymer comprises a polyethylenic backbone and wherein:
            (i) the first copolymerized monomer comprises a pendant moiety of the formula: —C(O)—O—(CH$_2$CH$_2$O)$_m$—Z, wherein:
            Z is H or alkyl of from 1 to 6 carbon atoms,
            m is 1 to 100;
            (ii) the second copolymerized monomer comprises a pendant moiety of the formula:
            —OC(O)NR-J wherein R is H or alkyl of from 1 to 6 carbon atoms and J is the member of a specific binding pair; and
            (iii) the third copolymerized monomer comprises a pendant moiety of the formula: —COOH or a derivative thereof,
   (b) subjecting the combination to conditions for forming a complex,
   (c) separating the solid support from the medium, and
   (d) activating the member of the signal producing system bound to the separated solid support and detecting the amount of the complex, the amount of the complex being related to the presence and/or amount of analyte in the sample.

3. The method according to claim 2 wherein the member of the signal producing system is selected from the group consisting of chemiluminescent compounds, fluorescent compounds, sensitizers, phosphorescent compounds, dyes and enzymes.

4. The method according to claim 2 wherein the member of the signal producing system is an acridinium ester.

5. The method according to claim 2 wherein the particle is a metal oxide particle wherein the metal is a paramagnetic metal selected from the group consisting of iron, lithium, sodium, magnesium, aluminum, manganese, strontium, zirconium, molybdenum, ruthenium, rhodium, palladium, tin, samarium, europium, tungsten, and platinum.

6. The method according to claim 2 wherein:
   The pendant moiety of the first copolymerized monomer is —C(O)—O—(CH$_2$CH$_2$O)$_m$—Z, wherein:
   Z is H or methyl and m is 1 to 100.

* * * * *